(12) United States Patent
Firminger et al.

(10) Patent No.: US 8,046,455 B2
(45) Date of Patent: Oct. 25, 2011

(54) CORRELATING SUBJECTIVE USER STATES WITH OBJECTIVE OCCURRENCES ASSOCIATED WITH A USER

(75) Inventors: Shawn P. Firminger, Redmond, WA (US); Jason Garms, Redmond, WA (US); Edward K. Y. Jung, Bellevue, WA (US); Chris D. Karkanias, Sammamish, WA (US); Eric C. Leuthardt, St. Louis, MO (US); Royce A. Levien, Lexington, MA (US); Robert W. Lord, Seattle, WA (US); Mark A. Malamud, Seattle, WA (US); John D. Rinaldo, Jr., Bellevue, WA (US); Clarence T. Tegreene, Bellevue, WA (US); Kristin M. Tolle, Redmond, WA (US); Lowell L. Wood, Jr., Bellevue, WA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 321 days.

(21) Appl. No.: 12/313,659

(22) Filed: Nov. 21, 2008

(65) Prior Publication Data

US 2010/0131471 A1    May 27, 2010

(51) Int. Cl.
*G06F 15/16* (2006.01)
*G06F 15/18* (2006.01)

(52) U.S. Cl. ........ 709/224; 709/206; 709/217; 707/755; 707/687; 707/736; 706/52; 706/46; 706/12; 706/11

(58) Field of Classification Search .................. 709/224, 709/206, 217
See application file for complete search history.

(56) References Cited

U.S. PATENT DOCUMENTS

| | | | |
|---|---|---|---|
| 3,599,149 A | 8/1971 | Pardoe | |
| 7,203,430 B2 * | 4/2007 | Ohta | ................................ 399/8 |
| 7,400,928 B2 | 7/2008 | Hatlestsad | |
| 7,627,544 B2 | 12/2009 | Chkodrov et al. | |
| 2003/0166277 A1 | 9/2003 | Zauderer et al. | |
| 2004/0103108 A1 | 5/2004 | Andreev et al. | |
| 2005/0102578 A1 | 5/2005 | Bliss et al. | |
| 2006/0034430 A1 | 2/2006 | Liakis | |

(Continued)

FOREIGN PATENT DOCUMENTS

WO    WO 99/18842    4/1999

OTHER PUBLICATIONS

Agger, Michael; "Every Day We Write the Book: What would happen if Facebook made its data available for research?"; Slate; bearing date of Nov. 30, 2010; printed on Dec. 10, 2010; pp. 1-3; located at: http://www.slate.com/formatdynamics/CleanPrintProxy.aspx?129200853368.

(Continued)

*Primary Examiner* — Jude Jean Gilles

(57) ABSTRACT

A computationally implemented method includes, but is not limited to: acquiring subjective user state data including at least a first subjective user state and a second subjective user state; acquiring objective context data including at least a first context data indicative of a first objective occurrence associated with a user and a second context data indicative of a second objective occurrence associated with the user; and correlating the subjective user state data with the objective context data. In addition to the foregoing, other method aspects are described in the claims, drawings, and text forming a part of the present disclosure.

45 Claims, 20 Drawing Sheets

U.S. PATENT DOCUMENTS

| | | | |
|---|---|---|---|
| 2007/0293731 | A1 | 12/2007 | Downs et al. |
| 2008/0034056 | A1 | 2/2008 | Renger et al. |
| 2008/0091515 | A1 | 4/2008 | Thieberger et al. |
| 2008/0215607 | A1 | 9/2008 | Kaushansky et al. |
| 2008/0218472 | A1 | 9/2008 | Breen et al. |
| 2009/0049154 | A1 | 2/2009 | Ge |
| 2009/0077658 | A1 | 3/2009 | King et al. |
| 2009/0132197 | A1 | 5/2009 | Rubin et al. |
| 2009/0240647 | A1 | 9/2009 | Green et al. |
| 2009/0276221 | A1 | 11/2009 | Heiman et al. |
| 2009/0326981 | A1 | 12/2009 | Karkanias et al. |
| 2010/0010866 | A1 | 1/2010 | Bal et al. |
| 2010/0088104 | A1 | 4/2010 | DeRemer et al. |

OTHER PUBLICATIONS

"Self-tracking links to get you started"; The Quantified Self: self knowledge through numbers; printed on Dec. 10, 2010; pp. 1-5; located at: http://quantifiedself.com/self-tracking-links-to-get-you-started/.

U.S. Appl. No. 12/462,201, Firminger et al.
U.S. Appl. No. 12/462,128, Firminger et al.
U.S. Appl. No. 12/459,854, Firminger et al.
U.S. Appl. No. 12/459,775, Firminger et al.
U.S. Appl. No. 12/456,433, Firminger et al.
U.S. Appl. No. 12/456,249, Firminger et al.
U.S. Appl. No. 12/455,317, Firminger et al.
U.S. Appl. No. 12/455,309, Firminger et al.
U.S. Appl. No. 12/387,487, Firminger et al.
U.S. Appl. No. 12/387,465, Firminger et al.
U.S. Appl. No. 12/384,779, Firminger et al.
U.S. Appl. No. 12/384,660, Firminger et al.
U.S. Appl. No. 12/383,817, Firminger et al.
U.S. Appl. No. 12/383,581, Firminger et al.
U.S. Appl. No. 12/380,573, Firminger et al.
U.S. Appl. No. 12/380,409, Firminger et al.
U.S. Appl. No. 12/378,288, Firminger et al.

Buchanan, Matt; "Twitter Toilet Tweets Your Poo"; gizmodo.com; bearing a date of May 18, 2009; pp. 1-2; located at http://gizmodo.com/5259381/twitter-toilet-tweets-your-poo; printed on Jul. 1, 2009.

Diaz, Jesus; "One Day, This Will Be Remembered as the First Real Tricorder"; gizmodo.com; bearing a date of Nov. 12, 2009; pp. 1-2; located at http://gizmodo.com/5403126/one-day-this-will-be-remembered-as-the...; printed on Nov. 25, 2009.

Fox, Stuart; "The John, 2.0"; Popular Science; bearing a date of May 18, 2009; pp. 1-2; located at http://www.popsci.con/scitech/article/2009-05/john-20; printed on Jul. 1, 2009.

Frucci, Adam; "SNIF Dog Tags Track What Your Dog Does All Day; Spoiler: Eat, Sleep, Poop"; gizmodo,com; bearing a date of Jun. 10, 2009; pp. 1-2; located at http://i.gizmodo.com/5286076/snif-dog-tags-track-what-your-dog-does-all-day-spoiler-eat-sl...; printed on Jul. 1, 2009.

Gross, Daniel; "A Jewish Mother in Your Cell Phone"; Slate; bearing a date of Nov. 10, 2009; pp. 1-3; located at http://www.slate.com/formatdynamics/CleanPringProxy.aspx?125919...; printed on Nov. 25, 2009.

"hacklab.Toilet—a twitter-enabled toilet at hacklab.to"; aculei.net; bearing a date of May 18, 2009; pp. 1-8; located at http://aculei.net/~shardy/hacklabtoilet/; printed on Jul. 1, 2009.

U.S. Appl. No. 12/378,162, Firminger et al.
U.S. Appl. No. 12/319,135, Firminger et al.
U.S. Appl. No. 12/319,134, Firminger et al.
U.S. Appl. No. 12/315,083, Firminger et al.

June, Laura; "Apple patent filing shows off activity monitor for skiers, bikers"; engadget.com; bearing a date of Jun. 11, 2009; pp. 1-8; located at http://www.engadget.com/2009/06/11/apple-patent-filing-shows-off-a...; printed on Jul. 1, 2009.

Kraft, Caleb; "Twittering toilet"; Hack A Day; bearing a date of May 5, 2009; pp. 1-11; located at http://hackaday.com/2009/05/05/twittering-toilet/; printed on Jul. 1, 2009.

"Mobile pollution sensors deployed"; BBC News; bearing a date of Jun. 30, 2009; pp. 1-2; located at http://news.bbc.co.uk/2/hi/science/nature/8126498.stm; printed on Jul. 1, 2009; © BBC MMIX.

Morales, C. Romero et al.; "Using sequential pattern mining for links recommendation in adaptive hypermedia educational systems"; Current Developments in Technology-Assisted Education; bearing a date of 2006; pp. 1016-1020; © FORMATEX 2006.

Nesbit, J.C. et al.; "Sequential pattern analysis software for educational event data"; pp. 1-5, 2006.

Oliver, Sam; "Apple developing activity monitor for skiers, snowboarders, bikers"; AppleInsider; bearing a date of Jun. 11, 2009; pp. 1-6; located at http://www.appleinsider.com/articles/09/06/11/apple_developing_act...; printed on Jul. 1, 2009; AppleInsider © 1997-2008.

Rettner, Rachael; "Cell Phones Allow Everyone to Be a Scientist"; LiveScience; bearing a date of Jun. 4, 2009; pp. 1-3; located at http://www.livescience.com/technology/090604-mobile-sensor.html; printed on Jul. 1, 2009; © Imaginova Corp.

SPSS; "Find patterns in data that identify combinations of events that occur together"; SPSS Association Rule Components; bearing a date of 2002; pp. 1-5; © 2002 SPSS Inc.

SPSS; "Find sequential patterns in data to predict events more accurately"; SPSS Sequence Association™ Component; bearing a date of 2002; pp. 1-5; © 2002 SPSS Inc.

Hansen, et al.; "Microblogging—Facilitating Tacit Knowledge?"—A Second Year Term Paper; Information Management Study at Copenhagen Business School; 2008; pp. 1-42; located at http://www.scribd.com/doc/3460679/Microblogging-as-a-Facilitator-for-Tacit-Knowledge.

Reiss, M.; "Correlations Between Changes in Mental States and Thyroid Activity After Different Forms of Treatment"; The British Journal of Psychology—Journal of Mental Science; bearing dates of Mar. 6, 1954 and 1954; pp. 687-703 [Abstract only provided]; located at http://bjp.rcpsych.org/cgi/content/abstract/100/420/687; The Royal College of Psychiatrists.

\* cited by examiner

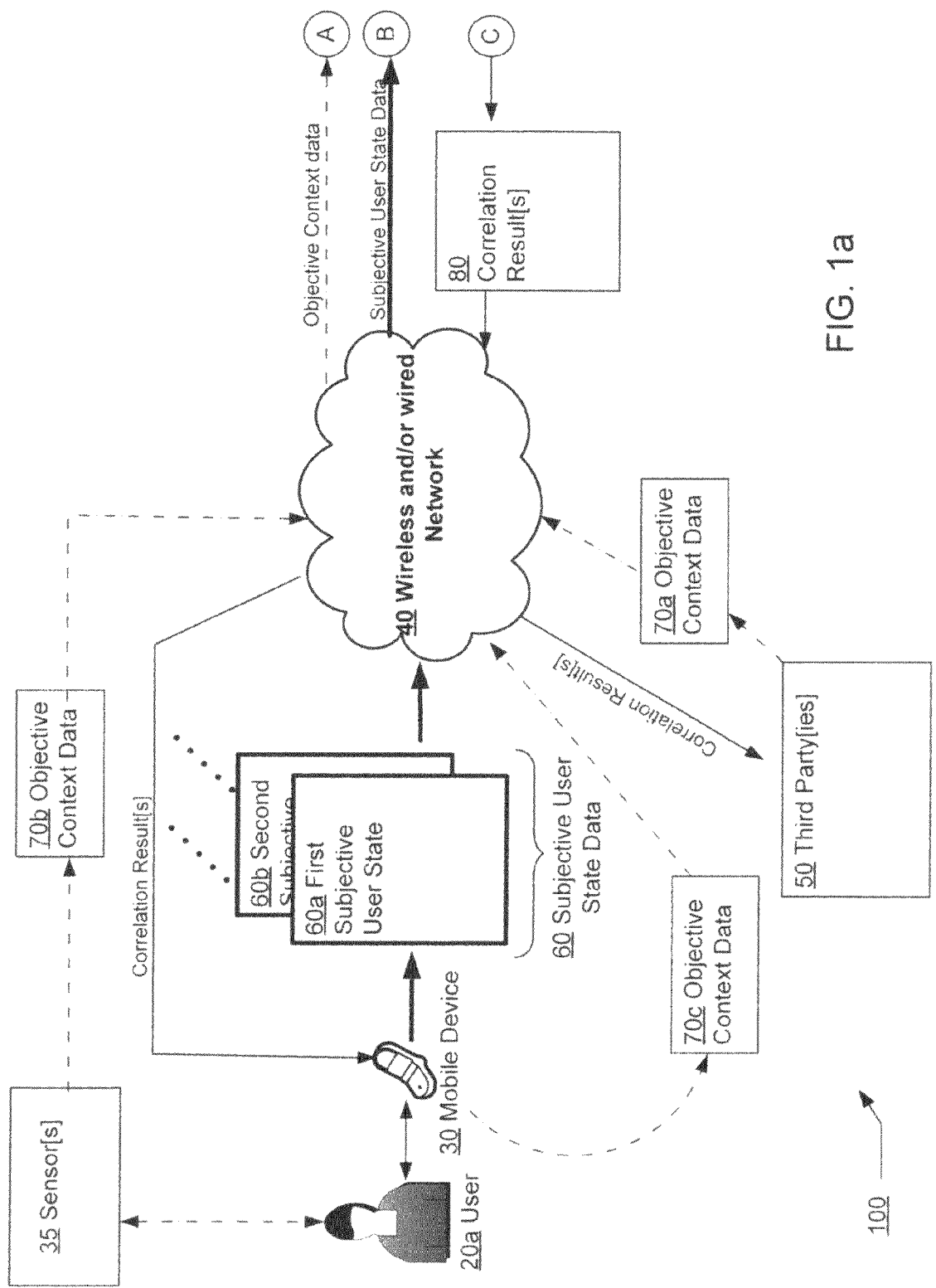

CORRELATING SUBJECTIVE USER STATES WITH OBJECTIVE OCCURRENCES ASSOCIATED WITH A USER

SUMMARY

A computationally implemented method includes, but is not limited to: acquiring subjective user state data including at least a first subjective user state and a second subjective user state; acquiring objective context data including at least a first context data indicative of a first objective occurrence associated with a user and a second context data indicative of a second objective occurrence associated with the user; and correlating the subjective user state data with the objective context data. In addition to the foregoing, other method aspects are described in the claims, drawings, and text forming a part of the present disclosure.

In one or more various aspects, related systems include but are not limited to circuitry and/or programming for effecting the herein-referenced method aspects; the circuitry and/or programming can be virtually any combination of hardware, software, and/or firmware configured to effect the herein-referenced method aspects depending upon the design choices of the system designer.

A computationally implemented system includes, but is not limited to: means for acquiring subjective user state data including at least a first subjective user state and a second subjective user state; means for acquiring objective context data including at least a first context data indicative of a first objective occurrence associated with a user and a second context data indicative of a second objective occurrence associated with the user; and means for correlating the subjective user state data with the objective context data. In addition to the foregoing, other system aspects are described in the claims, drawings, and text forming a part of the present disclosure.

A computationally implemented system includes, but is not limited to: circuitry for acquiring subjective user state data including at least a first subjective user state and a second subjective user state; circuitry for acquiring objective context data including at least a first context data indicative of a first objective occurrence associated with a user and a second context data indicative of a second objective occurrence associated with the user; and circuitry for correlating the subjective user state data with the objective context data. In addition to the foregoing, other system aspects are described in the claims, drawings, and text forming a part of the present disclosure.

A computer program product including a signal-bearing medium bearing one or more instructions for acquiring subjective user state data including at least a first subjective user state and a second subjective user state; one or more instructions for acquiring objective context data including at least a first context data indicative of a first objective occurrence associated with a user and a second context data indicative of a second objective occurrence associated with the user; and one or more instructions for correlating the subjective user state data with the objective context data. In addition to the foregoing, other computer program product aspects are described in the claims, drawings, and text forming a part of the present disclosure.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIGS. 1a and 1b show a high-level block diagram of a network device operating in a network environment.

DETAILED DESCRIPTION

Figure 1B:
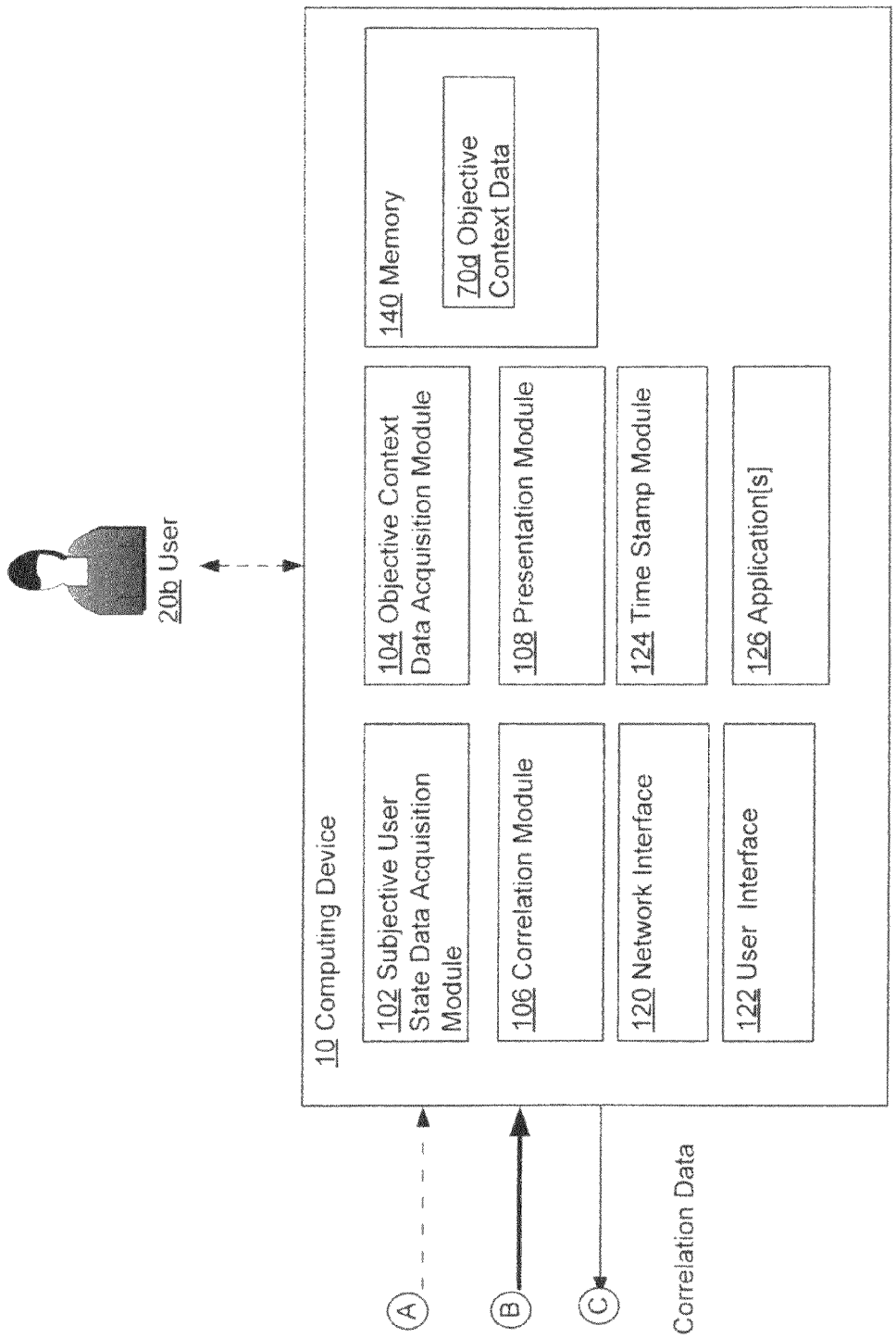

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

A recent trend that is becoming increasingly popular in the computing/communication field is to electronically record one's feelings, thoughts, and other aspects of the person's everyday life onto an open diary. One place where such open diaries are maintained are at social networking sites commonly known as "blogs" where one or more users may report or post the latest news, their thoughts and opinions on various topics, and various aspects of the users' everyday life. The process of reporting or posting blog entries is commonly referred to as blogging. Other social networking sites may allow users to update their personal information via social network status reports in which a user may report or post for others to view the latest status or other aspects of the user.

A more recent development in social networking is the introduction and explosive growth of microblogs in which individuals or users (referred to as "microbloggers") maintain open diaries at microblog websites (e.g., otherwise known as "twitter") by continuously or semi-continuously posting microblog entries. A microblog entry (e.g., "tweet") is typically a short text message that is usually not more than 140 characters long. The microblog entries posted by a microblogger may report on any aspect of the microblogger's daily life.

The various things that are typically posted though microblog entries may be categorized into one of at least two possible categories. The first category of things that may be reported through microblog entries are "objective occurrences" associated with the microblogger (e.g., "user"). Objective occurrences associated with the microblogger (e.g., user) may be any characteristic, event, happening, or aspect associated with or is of interest to the microblogger that can be objectively reported by the microblogger, a third party, or by a device. These things would include, for example, food, medicine, or nutraceutical intake of the microblogger, certain physical characteristics of the microblogger such as blood sugar level or blood pressure that can be objectively measured, daily activities of the microblogger observable by others or by a device, the local weather, the stock market (which the microblogger may have an interest in), activities of others (e.g., spouse or boss) that may directly or indirectly affect the microblogger, and so forth.

A second category of things that may be reported or posted through microblogging entries include "subjective states" of the microblogger (e.g., user). Subjective states of a microblogger (e.g., a user) include any subjective state or status associated with the microblogger that can only be typically reported by the microblogger (e.g., generally cannot be reported by a third party or by a device). Such states including, for example, the mental state of the microblogger (e.g., "I am feeling happy"), particular physical states of the microblogger (e.g., "my ankle is sore" or "my ankle does not hurt anymore" or "my vision is blurry"), and overall state of the microblogger (e.g., "I'm good" or "I'm well"). Although microblogs are being used to provide a wealth of personal information, they have only been primarily limited to their use as a means for providing commentaries and for maintaining open diaries.

In accordance with various embodiments, methods, systems, and computer program products are provided for correlating subjective user state data (e.g., data that indicate subjective user states of a user) with objective context data (e.g., data that indicate objective occurrences associated with the user). In other words, to determine a causal relationship between objective occurrences (e.g., cause) and subjective user states (e.g., result) associated with a user (e.g., a blogger or microblogger). For example, determining that whenever a user eats a banana (e.g., objective occurrence) the user feels "good" (e.g., subjective user state). Note that an objective occurrence does not need to precede a corresponding subjective user state. For example, a person may become "gloomy" (e.g., subjective user state) whenever it is about to rain (e.g., objective occurrence).

As will be used herein a "subjective user state" is in reference to any state or status associated with a user (e.g., a blogger or microblogger) that only the user can typically indicate or describe. Such states include, for example, the subjective mental state of the user (e.g., user is feeling sad), a subjective physical state (e.g., physical characteristic) that only the user can typically indicate (e.g., a backache or an easing of a backache as opposed to blood pressure which can be reported by a blood pressure device and/or a third party), or the subjective overall state of the user (e.g., user is "good"). Examples of subjective mental states include, for example, happiness, sadness, depression, anger, frustration, elation, fear, alertness, sleepiness, and so forth. Examples of subjective physical states include, for example, the presence, easing, or absence of pain, blurry vision, hearing loss, upset stomach, physical exhaustion, and so forth. Subjective overall states may include any subjective user states that cannot be categorized as a subjective mental state or as a subjective physical state. Examples of overall states of a user that may be subjective user states include, for example, user being good, bad, exhausted, lack of rest, user wellness, and so forth.

In contrast, "objective context data" may include data that indicate objective occurrences associated with the user. An objective occurrence may be any physical characteristic, event, happenings, or aspects associated with or is of interest to a user that can be objectively reported by at least a third party or a sensor device. Note, however, that such objective context data does not have to be actually provided by a sensor device or by a third party, but instead, may be reported by the user himself or herself (e.g., via microblog entries). Examples of objectively reported occurrences that could by indicated by the objective context data include, for example, a user's food, medicine, or nutraceutical intake, the user's location at any given point in time, the user's exercise routine, user's blood pressure, the weather at user's location, activities associated with third parties, the stock market, and so forth.

The term "correlating" as will be used herein is in reference to a determination of one or more relationships between at least two variables. In the following exemplary embodiments, the first variable is subjective user state data that represents at least a first and a second subjective user state of a user and the second variable is objective context data that represents at least a first and a second objective occurrence associated with the user. Note that each of the at least first and second subjective user states represented by the subjective user state data may represent the same or similar type of subjective user state (e.g., user feels happy) but may be distinct subjective user states because they occurred at different points in time (e.g., user feels happy during a point in time and the user being happy again during another point in time). Similarly, each of the first and second objective occurrences represented by the objective context data may represent the same or similar type of objective occurrence (e.g., user eating a banana) but may be distinct objective occurrences because they occurred at different points in time (e.g., user ate a banana during a point in time and the user eating another banana during another point in time).

Various techniques may be employed for correlating the subjective user state data with the objective context data. For example, in some embodiments, correlating the objective context data with the subjective user state data may be accomplished by determining time sequential patterns or relationships between reported objective occurrences associated with a user and reported subjective user states of the user.

The following illustrative example is provided to describe how subjective user states and objective occurrences associated with a user may be correlated according to some embodiments. Suppose, for example, a user such as a microblogger reports that the user ate a banana on a Monday. The consumption of the banana, in this example, is a reported first objective occurrence associated with the user. The user then reports that 15 minutes after eating the banana, the user felt very happy. The reporting of the emotional state (e.g., felt very happy) is, in this example, a reported first subjective user state. On Tuesday, the user reports that the user ate another banana (e.g., a second objective occurrence associated with the user). The user then reports that 15 minutes after eating the second banana, the user felt somewhat happy (e.g., a second subjective user state). For purposes of this example, the reporting of the consumption of the bananas may be in the form of objective context data and the reporting of the user feeling very or somewhat happy may be in the form of subjective user state data. The reported information may then be examined from different perspectives in order to determine whether there is a correlation (e.g., relationship) between the subjective user state data indicating the subjective user states (e.g., happiness of the user) and the objective context data indicating the objective occurrences associated with the user (e.g., eating bananas).

Several approaches may be employed in various alternative implementations in order to determine whether there is correlation (e.g., a relationship) between the subjective user state data and the objective context data. For example, a determination may be made as to whether there is co-occurrence, temporal sequencing, temporal proximity, and so forth, between the subjective user states (e.g., as provided by the subjective user state data) and the objective occurrences (e.g., as provided by the objective context data) associated with the user. One or more factors may be relevant in the determination of whether there is correlation between the subjective user state data and the objective context data.

One factor that may be examined in order to determine whether a relationship exists between the subjective user state data (e.g., happiness of the user) and the objective context data (e.g., consumption of bananas) is whether the first and second objective occurrences (e.g., consuming a banana) of the user are the same or similar (e.g., extent of similarity or difference). In this case, the first and second objective occurrences are the same. Note that consumption of the bananas could have been further defined. For example, the quantity or the type of bananas consumed could have been specified. If the quantity or the type of bananas consumed were not the same, then this could negatively impact the correlation (e.g., determination of a relationship) of the subjective user state data (e.g., happiness of the user) with the objective context data (e.g., eating bananas).

Another relevant factor that could be examined is whether the first and second subjective user states of the user are the same or similar (e.g., extent of similarity or difference). In this case, the first subjective user state (e.g., felt very happy) and second subjective user states (e.g., felt somewhat happy) are not the same but are similar. In this case, the comparison of the two subjective user states indicates that the two subjective user states, although not the same, are similar. This may result ultimately in a determination of a weaker correlation between the subjective user state data and the objective context data.

A third relevant factor that may be examined is whether the time difference between the first subjective user state and the first objective occurrence associated with the user (e.g., 15 minutes) and the time difference between the second subjective user state and the second objective occurrence associated with the user (e.g., 15 minutes) are the same or similar. In this case, the time difference between the first subjective user state and the first objective occurrence associated with the user (e.g., 15 minutes) and the time difference between the second subjective user state and the second objective occurrence associated with the user (e.g., 15 minutes) are indeed the same. As a result, this may indicate a relatively strong correlation between the subjective user state data (e.g., happiness of the user) and the objective context data (e.g., eating of bananas by the user). This operation is a relatively simple way of determining time sequential patterns. Note that if the time difference between the first subjective user state and the first objective occurrence associated with the user and the time difference between the second subjective user state and the second objective occurrence associated with the user (e.g., 15 minutes) were not the same or not similar, a weaker correlation or no correlation between the subjective user state data (e.g., happiness of the user) and the objective context data (e.g., eating of bananas by the user) may be concluded. Further, if the time differences were large (e.g., there was a four hour gap between the reporting of a consumption of a banana and the feeling of happiness), then this may indicate a weaker correlation between the subjective user state data (e.g., happiness of the user) and the objective context data (e.g., eating of bananas by the user).

The review of the subjective user state data and the objective context data from these perspectives may facilitate in determining whether there is a correlation between such data. That is, by examining such data from the various perspectives as described above, a determination may be made as to whether there is a sequential relationship between subjective user states (e.g., happiness of the user) and objective occurrences (e.g., consumption of bananas) associated with the user. Of course, those skilled in the art will recognize that the correlation of subjective user state data with objective context data may be made with greater confidence if more data points are obtained. For instance, in the above example, a stronger relationship may be determined between the subjective user state data (e.g., happiness of the user) and the objective context data (e.g., consumption of bananas) if additional data points with respect to the subjective user state data (e.g., a third subjective user state, a fourth subjective user state, and so forth) and the objective context data (e.g., a third objective occurrence, a fourth objective occurrence, and so forth) were obtained and analyzed.

In alternative embodiments, other techniques may be employed in order to correlate subjective user state data with objective context data. For example, one approach is to determine whether a subjective user state repeatedly occurres before, after, or at least partially concurrently with an objective occurrence. For instance, a determination may be made as to whether a user repeatedly has a stomach ache (e.g., subjective user state) each time after eating a banana (e.g., objective occurrence). In another example, a determination may be made as to whether a user repeatedly feels gloomy (e.g., subjective user state) before each time it begins to rain (e.g., objective occurrence). In still another example, a determination may be made as to whether a user repeatedly feels happy (e.g., subjective user state) each time his boss leaves town (e.g., objective occurrence).

FIGS. 1a and 1b illustrate an example environment in accordance with various embodiments. In the illustrated environment, an exemplary system 100 may include at least a computing device 10 (see FIG. 1b) that may be employed in order to, among other things, collect subjective user state data 60 and objective context data 70* that are associated with a user 20*, and to correlate the subjective user state data 60 with the objective context data 70*. Note that in the following, "*" indicates a wildcard. Thus, user 20* may indicate a user 20a or a user 20b of FIGS. 1a and 1b.

In some embodiments, the computing device 10 may be a network server in which case the computing device 10 may communicate with a user 20a via a mobile device 30 and through a wireless and/or wired network 40. Note that a network server as described herein may be in reference to a network server located at a single network site or located across multiple network sites or a conglomeration of servers located at multiple network sites. The mobile device 30 may be a variety of computing/communication devices including, for example, a cellular phone, a personal digital assistant (PDA), a laptop, or some other type of mobile computing/communication device. In alternative embodiments, the computing device 10 may be a local computing device that communicates directly with a user 20b. For these embodiments, the computing device 10 may be any type of handheld device such as a cellular telephone or a PDA, or other types of computing/communication devices such as a laptop computer, a desktop computer, and so forth. In certain embodiments, the computing device 10 may be a peer-to-peer network component device. In some embodiments, the local device 30 may operate via web 2.0 construct.

In embodiments where the computing device 10 is a server, the computing device 10 may indirectly obtain the subjective user state data 60 from a user 20a via the mobile device 30. In alternative embodiments in which the computing device 10 is a local device, the subjective user state data 60 may be directly obtained from a user 20b. As will be further described, the computing device 10 may acquire the objective context data 70* from one or more different sources.

For ease of illustration and explanation, the following systems and operations to be described herein will be generally described in the context of the computing device 10 being a network server. However, those skilled in the art will recognize that these systems and operations may also be implemented when the computing device 10 is a local device communicating directly with a user 20b.

Assuming that the computing device 10 is a server, the computing device 10 may be configured to acquire subjective user state data 60 including data indicating at least a first subjective user state 60a and a second subjective user state 60b via the mobile device 30 and through wireless and/or wired networks 40. In some embodiments, the data indicating the first subjective user state 60a and the second subjective user state 60b may be in the form of blog entries, such as microblog entries, or embodied in some other form of electronic messages. The first subjective user state 60a and the second subjective user state 60b may, in some instances, indicate the same, similar, or completely different subjective user state. Examples of subjective user states indicated by the first subjective user state 60a and the second subjective user state 60b include, for example, a subjective mental state of the user 20a (e.g., user 20a is sad or angry), a subjective physical state of the user 20a (e.g., physical or physiological characteristic of the user 20a such as the presence or absence of a stomach ache or headache), a subjective overall state of the user 20a (e.g., user is "well"), or other subjective user states that only the user 20a can typically indicate.

The computing device 10 may be further configured to acquire objective context data 70* from one or more sources. For instance, objective context data 70a may be acquired, in some instances, from one or more third parties 50 (e.g., other users, a health care provider, a hospital, a place of employment, a content provider, and so forth). In some alternative situations, objective context data 70b may be acquired from one or more sensors 35 (e.g., blood pressure device or glucometer) sensing, for example, one or more physical characteristics of the user 20a. Note that the one or more sensors 35 may be other types of sensors for measuring and providing to the computing device 10 other subjective occurrences associated with user 20a. For example, in some cases, sensors 35 may include a global positioning system (GPS) device for determining the location of the user 20a or a physical activity sensor for measuring physical activities of the user 20a. Examples of a physical activity sensor include, for example, a pedometer for measuring physical activities of the user 20a. In some implementations, the one or more sensors 35 may include one or more physiological sensor devices for measuring physiological characteristics of the user 20a. Examples of physiological sensor devices include, for example, a blood pressure monitor, a heart rate monitor, a glucometer, and so forth. In some implementations, the one or more sensors 35 may include one or more image capturing devices such as a video or digital camera.

In still other situations, objective context data 70c may be acquired from the user 20a via the mobile device 30. For these situations, the objective context data 70c may indicate, for example, activities (e.g., exercise or food or medicine intake) performed by the user 20a, certain physical characteristics (e.g., blood pressure or location) associated with the user 20a, or other aspects associated with the user 20a that the user 20a can report objectively. In still other alternative cases, objective context data 70d may be acquired from a memory 140.

In various embodiments, the context data 70* acquired by the computing device 10 may include at least a first context data indicative of a first objective occurrence associated with the user 20a and a second context data indicative of a second objective occurrence associated with the user 20a. In some implementations, the first and second context data may be acquired in the form of blog entries (e.g., microblog entries) or in other forms of electronic messages.

The computing device 10 may be further configured to correlate the acquired subjective user data 60 with the acquired context data 70*. By correlating the acquired subjective user data 60 with the acquired context data 70*, a determination may be made as to whether there is a relationship between the acquired subjective user data 60 with the acquired context data 70*. In some embodiments, and as will be further indicated in the operations and processes to be described herein, the computing device 10 may be further configured to present one or more the results of correlation. In various embodiments, the one or more correlation results 80 may be presented to the user 20a and/or to one or more third parties 50. The one or more third parties 50 may be other users such as other microbloggers, a health care provider, advertisers, and/or content providers.

As illustrated in FIG. 1b, computing device 10 may include one or more components or sub-modules. For instance, in various implementations, computing device 10 may include a subjective user state data acquisition module 102, an objective context data acquisition module 104, a correlation module 106, a presentation module 108, a network interface 120, a user interface 122, a time stamp module 124, one or more applications 126, and/or memory 140. The functional roles of these components/modules will be described in the processes and operations to be described herein.

Figure 2A:
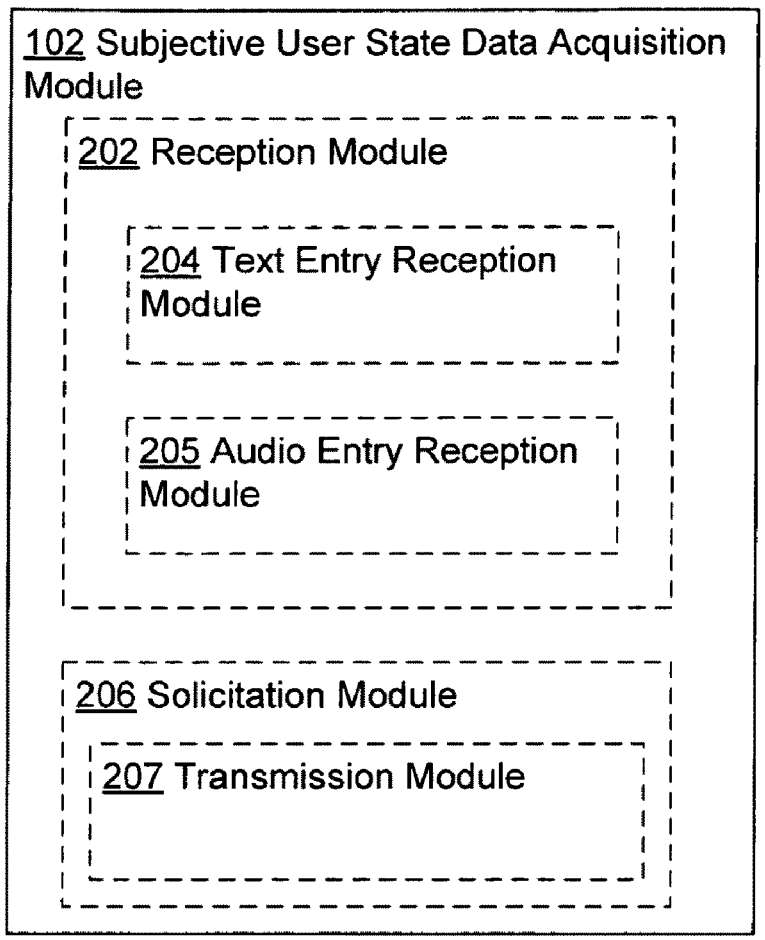
FIG. 2a shows another perspective of the subjective user state data acquisition module 102 of the computing device 10 of FIG. 1b.

FIG. 2a illustrates particular implementations of the subjective user state data acquisition module 102 of the computing device 10 of FIG. 1b. In brief, the subjective user state data acquisition module 102 may be designed to, among other things, acquire subjective user state data 60 including at least a first subjective user state 60a and a second subjective user state 60b. As further illustrated, the subjective user state data acquisition module 102 in various implementations may include a reception module 202 for receiving the subjective user state data 60 from a user 20a via the network interface 120 or for receiving the subjective user state data 60 directly from a user 20b (e.g., in the case where the computing device 10 is a local device) via the user interface 122.

In some implementations, the reception module 202 may further include a text entry reception module 204 for receiving subjective user state data that was obtained based, at least in part, on a text entry provided by a user 20*. For example, in some implementations the text entry reception module 204 may be designed to receive subjective user state data 60 that was obtained based, at least in part, on a text entry (e.g., a text microblog entry) provided by a user 20a using a mobile device 30. In an alternative implementation or the same implementation, the reception module 202 may include an audio entry reception module 205 for receiving subjective user state data that was obtained based, at least in part, on an audio entry provided by a user 20*. For example, in some implementations the audio entry reception module 205 may be designed to receive subjective user state data 60 that was obtained based, at least in part, on an audio entry (e.g., an audio microblog entry) provided by a user 20a using a mobile device 30.

In some implementations, the subjective user state data acquisition module 102 may include a solicitation module 206 for soliciting from a user 20* a subjective user state. For example, the solicitation module 206, in some implementations, may be designed to solicit from a user 20b, via a user interface 122 (e.g., in the case where the computing device 10 is a local device), a subjective user state of the user 20b (e.g., whether the user 20b is feeling very good, good, bad, or very bad). The solicitation module 206 may further include a transmission module 207 for transmitting to a user 20a a request requesting a subjective user state 60*. For example, the transmission module 207 may be designed to transmit to a user 20a, via a network interface 122, a request requesting a subjective user state 60*. The solicitation module 206 may be used in some circumstances in order to prompt the user 20* to provide useful data. For instance, if the user 20* has reported a first subjective user state 60a following a first objective occurrence, then the solicitation module 206 may solicit from the user 20* a second subjective user state 60b following the happening of the second objective occurrence.

Figure 2B:
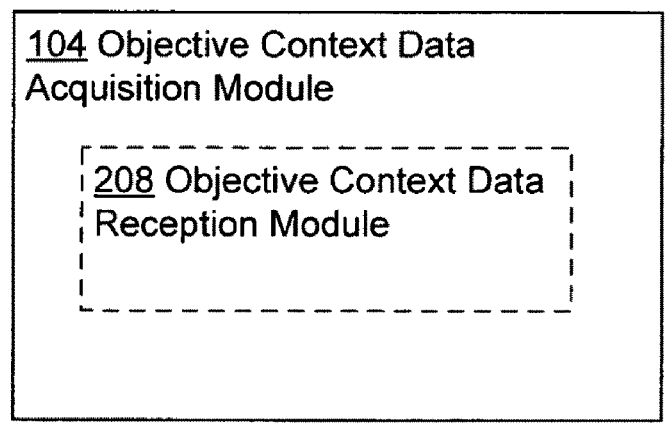
FIG. 2b shows another perspective of the objective context data acquisition module 104 of the computing device 10 of FIG. 1b.

Referring now to FIG. 2b illustrating particular implementations of the objective context data acquisition module 104 of the computing device 10 of FIG. 1b. In various implementations, the objective context data acquisition module 104 may be configured to acquire (e.g., either receive, solicit, or retrieve from a user 20*, a third party 50, a sensor 35, and/or a memory 140) objective context data 70* including at least a first context data indicative of a first objective occurrence associated with a user 20* and a second context data indicative of a second objective occurrence associated with the user 20*. In some implementations, the objective context data acquisition module 104 may include an objective context data reception module 208 that is configured to receive objective context data 70*. For example, the objective context data reception module 208 may be designed to receive, via a user interface 122 or a network interface 120, context data from a user 20*, from a third party 50, and/or from a sensor 35.

Figure 2C:
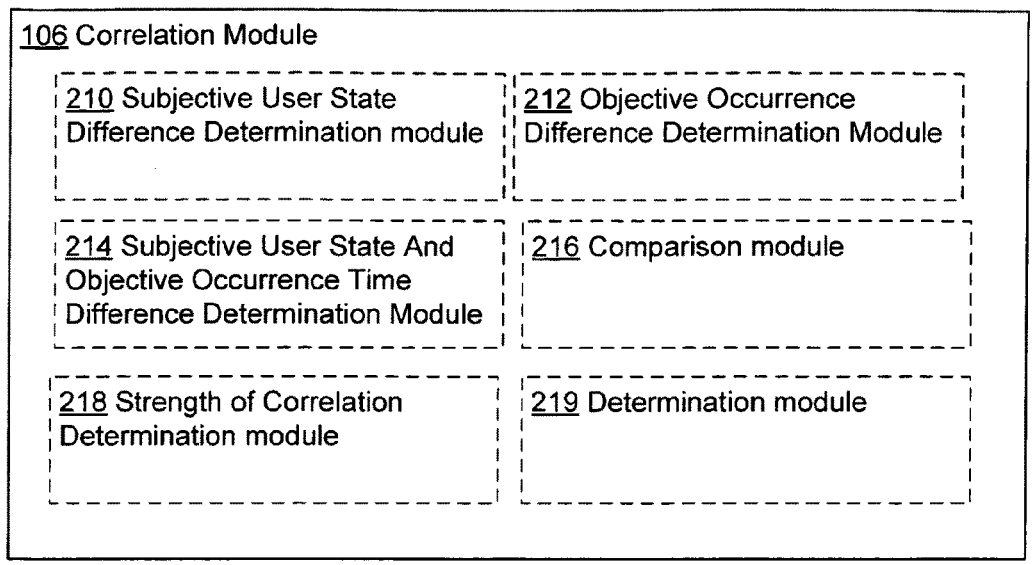
FIG. 2c shows another perspective of the correlation module 106 of the computing device 10 of FIG. 1b.

Turning now to FIG. 2c illustrating particular implementations of the correlation module 106 of the computing device 10 of FIG. 1b. The correlation module 106 may be configured to, among other things, correlate subjective user state data 60 with objective context data 70*. In some implementations, the correlation module 106 may include a subjective user state difference determination module 210 for determining an extent of difference between a first subjective user state 60a and a second subjective user state 60b associated with a user 20*. In the same or different implementations, the correlation module 106 may include a objective occurrence difference determination module 212 for determining an extent of difference between at least a first objective occurrence and a second objective occurrence associated with a user 20*.

In the same or different implementations, the correlation module 106 may include a subjective user state and objective occurrence time difference determination module 214. As will be further described below, the subjective user state and objective occurrence time difference determination module 214 may be configured to determine at least an extent of time difference between a subjective user state associated with a user 20* and an objective occurrence associated with the user 20*. In the same or different implementations, the correlation module 106 may include a comparison module 216 for comparing an extent of time difference between a first subjective user state and a first objective occurrence associated with a user 20* with the extent of time difference between a second subjective user state and a second objective occurrence associated with the user 20*.

In the same or different implementations, the correlation module 106 may include a strength of correlation determination module 218 for determining a strength of correlation between subjective user state data and objective context data associated with a user 20*. In some implementations, the strength of correlation may be determined based, at least in part, on results provided by the objective occurrence difference determination module 210, the objective occurrence difference determination module 212, the subjective user state and objective occurrence time difference determination module 214 and/or the comparison module 216. In some implementations, and as will be further described herein, the correlation module 106 may include a determination module 219 for determining whether a subjective user state occurred before, after, or at least partially concurrently with an objective occurrence associated with a user 20*.

Figure 2D:
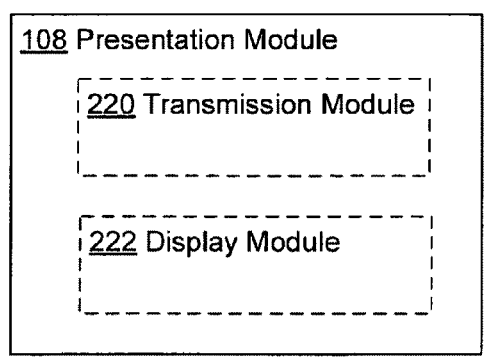
FIG. 2d shows another perspective of the presentation module 108 of the computing device 10 of FIG. 1b.

FIG. 2d illustrates particular implementations of the presentation module 108 of the computing device 10 of FIG. 1b. In various implementations, the presentation module 108 may be configured to present one or more results of the correlation performed by the correlation module 106. For example, in some implementations this may entail the presentation module 108 presenting to the user 20* an indication of a sequential relationship between a subjective user state and an objective occurrence associated with the user 20* (e.g., "whenever you eat a banana, you have a stomachache). Other types of results may also be presented in other alternative implementations as will be further described herein.

In various implementations, the presentation module 108 may include a transmission module 220 for transmitting one or more results of the correlation performed by the correlation module 106. For example, in the case where the computing device 10 is a server, the transmission module 220 may be configured to transmit to the user 20a or a third party 50 the one or more results of the correlation performed by the correlation module 106 via a network interface 120.

In some alternative implementations, the presentation module may include a display module 222 for displaying the one or more results of the correlation performed by the correlation module 106. For example, in the case where the computing device 10 is a local device, the display module 222 may be configured to display to the user 20*b* the one or more results of the correlation performed by the correlation module 106 via a user interface 122.

Referring back to FIG. 1*b*, and as briefly described earlier, in some implementations, the computing device 10 may include a time stamp module 124. For these implementations, the time stamp module 124 may be configured to provide time stamps for objective occurrences and/or subjective user states associated with a user 20*. For example, if the computing device 10 is a local device that communicates directly with a user 20*a*, then the time stamp module 124 may generate a first time stamp for the first subjective user state 60*a* and a second time stamp for the second subjective user state 60*b*. Note that the time stamps provided by the time stamp module 124 may be associated with subjective user states and/or objective occurrences rather than being associated with subjective user state data 60 and/or objective context data. 70*. That is, the times in which the subjective user states and/or the objective occurrences occurred may be more relevant than when these events were actually reported (e.g., reported via microblog entries).

In various embodiments, the computing device 10 may include a network interface 120 that may facilitate in communicating with a user 20*a* and/or one or more third parties 50. For example, in embodiments whereby the computing device 10 is a server, the computing device 10 may include a network interface 120 that may be configured to receive from the user 20*a* subjective user state data 60. In some embodiments, objective context data 70*a*, 70*b*, or 70*c* may be received through the communication interface 120. Examples of a network interface 120 includes, for example, a network interface card (NIC).

In various embodiments, the computing device 10 may include a user interface 122 to communicate directly with a user 20*b*. For example, in embodiments in which the computing device 10 is a local device, the user interface 122 may be configured to directly receive from the user 20*b* subjective user state data 60. The user interface 122 may include, for example, one or more of a display monitor, a touch screen, a key board, a mouse, an audio system, and/or other user interface devices.

Figure 2E:
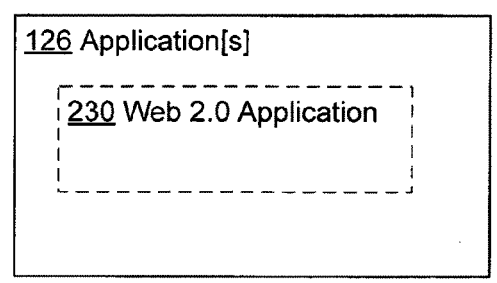
FIG. 2e shows another perspective of the one or more applications 126 of the computing device 10 of FIG. 1b.

FIG. 2*e* illustrates particular implementations of the one or more applications 126 of FIG. 1*b*. For these implementations, the one or more applications 126 may include, for example, communication applications such as a text messaging application and/or an audio messaging application including a voice recognition system application. In some implementations, the one or more applications 126 may include a web 2.0 application 230 to facilitate communication via, for example, the World Wide Web.

Figure 3:
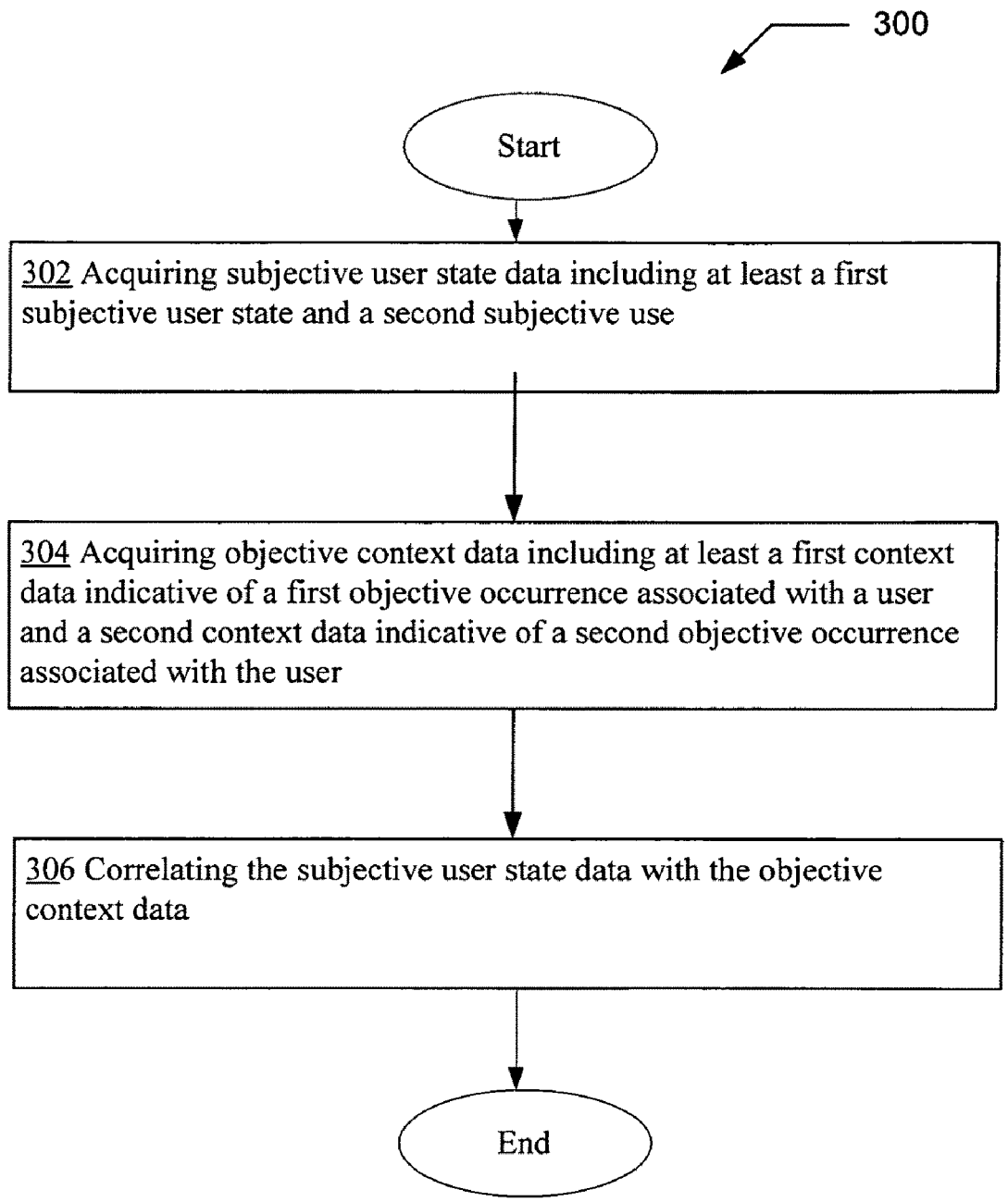
FIG. 3 is a high-level logic flowchart of a process.

FIG. 3 illustrates an operational flow 300 representing example operations related to acquisition and correlation of subjective user state data and objective context data in accordance with various embodiments. In some embodiments, the operational flow 300 may be executed by, for example, the computing device 10 of FIG. 1*b*.

In FIG. 3 and in the following figures that include various examples of operational flows, discussions and explanations may be provided with respect to the above-described exemplary environment of FIGS. 1*a* and 1*b*, and/or with respect to other examples (e.g., as provided in FIGS. 2*a*-2*e*) and contexts. However, it should be understood that the operational flows may be executed in a number of other environments and contexts, and/or in modified versions of FIGS. 1*a*, 1*b*, and 2*a*-2*e*. Also, although the various operational flows are presented in the sequence(s) illustrated, it should be understood that the various operations may be performed in other orders than those which are illustrated, or may be performed concurrently.

Further, in FIG. 3 and in following figures, various operations may be depicted in a box-within-a-box manner. Such depictions may indicate that an operation in an internal box may comprise an optional example embodiment of the operational step illustrated in one or more external boxes. However, it should be understood that internal box operations may be viewed as independent operations separate from any associated external boxes and may be performed in any sequence with respect to all other illustrated operations, or may be performed concurrently.

In any event, after a start operation, the operational flow 300 may move to a subjective user state data acquisition operation 302 for acquiring subjective user state data including at least a first subjective user state and a second subjective user state as performed by, for example, the computing device 10 of FIG. 1*b*. For instance, the subjective user state data acquisition module 102 of the computing device 10 acquiring subjective user state data 60 (e.g., in the form of text or audio microblog entries) including at least a first subjective user state 60*a* (e.g., the user 20* is feeling sad) and a second subjective user state 60*b* (e.g., the user 20* is again feeling sad).

Operational flow 300 further includes an objective context data acquisition operation 304 for acquiring objective context data including at least a first context data indicative of a first objective occurrence associated with a user and a second context data indicative of a second objective occurrence associated with the user as performed by, for example, the computing device 10. For instance, the objective context data acquisition module 104 of the computing device 10 acquiring via a wireless and/or wired network 40 objective context data 70* (e.g., as provided by a third party source or by the user 20*a*) including at least a first context data 70* indicative of a first occurrence (e.g., cloudy weather) associated with a user 20* and a second context data 70* indicative of a second occurrence (e.g., cloudy weather) associated with the user 20*. Note that, and as those skilled in the art will recognize, the subjective user state data acquisition operation 302 does not have to be performed prior to the objective context data acquisition operation 304 and may be performed subsequent to the performance of the objective context data acquisition operation 304 or may be performed concurrently with the objective context data acquisition operation 304.

Finally, a correlation operation 306 for correlating the subjective user state data with the objective context data may be performed by, for example, the computing device 10. For instance, the correlation module 106 of the computing device 10 correlating the subjective user state data 60 with the objective context data 70* by determining a sequential time relationship between the subjective user state data 60 and the objective context data 70* (e.g., user 20* will be sad whenever it is cloudy).

Figure 4A:
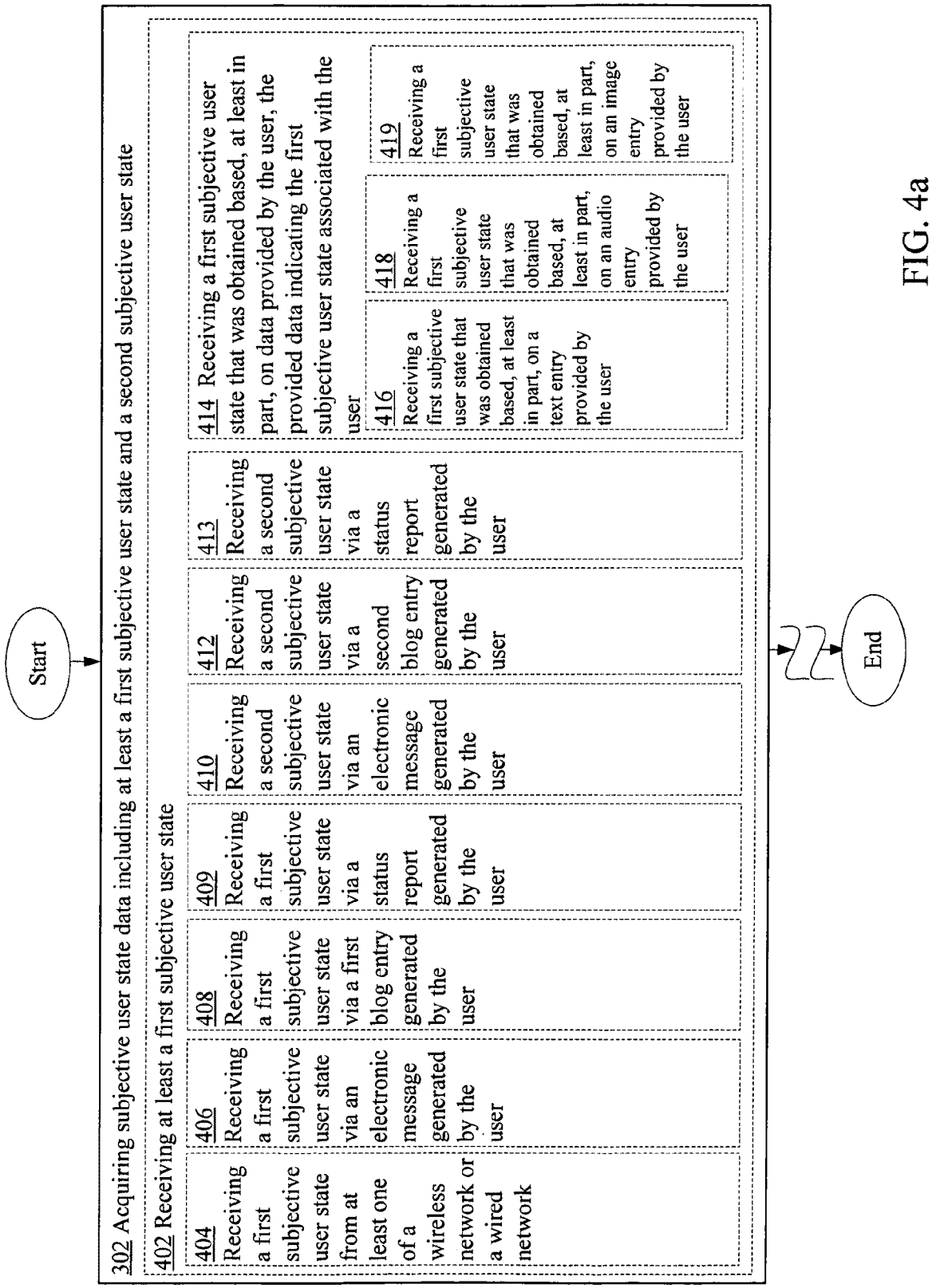
FIG. 4a is a high-level logic flowchart of a process depicting alternate implementations of the subjective user state data acquisition operation 302 of FIG. 3.
Figure 4B:
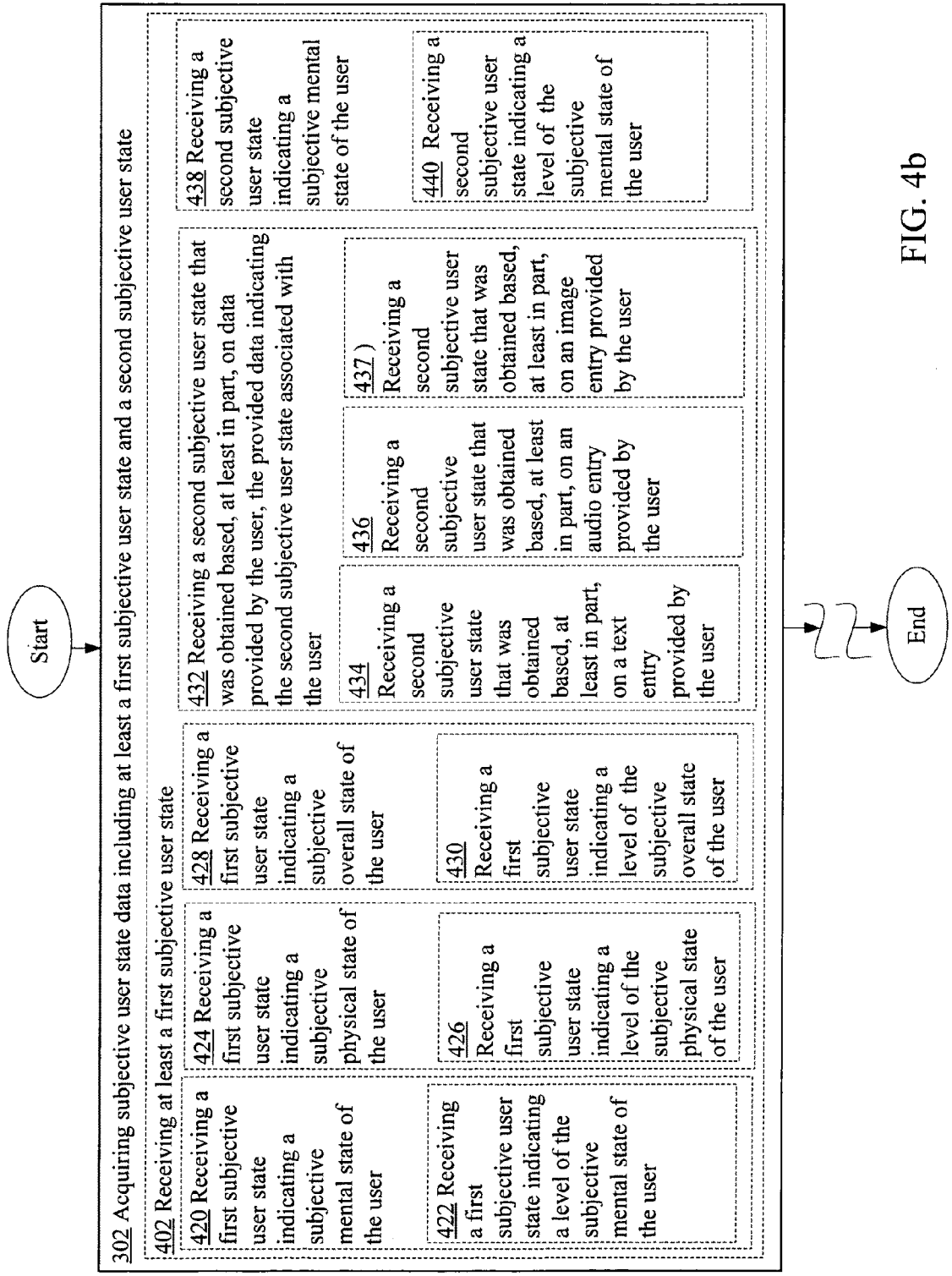
FIG. 4b is a high-level logic flowchart of a process depicting alternate implementations of the subjective user state data acquisition operation 302 of FIG. 3.
Figure 4C:
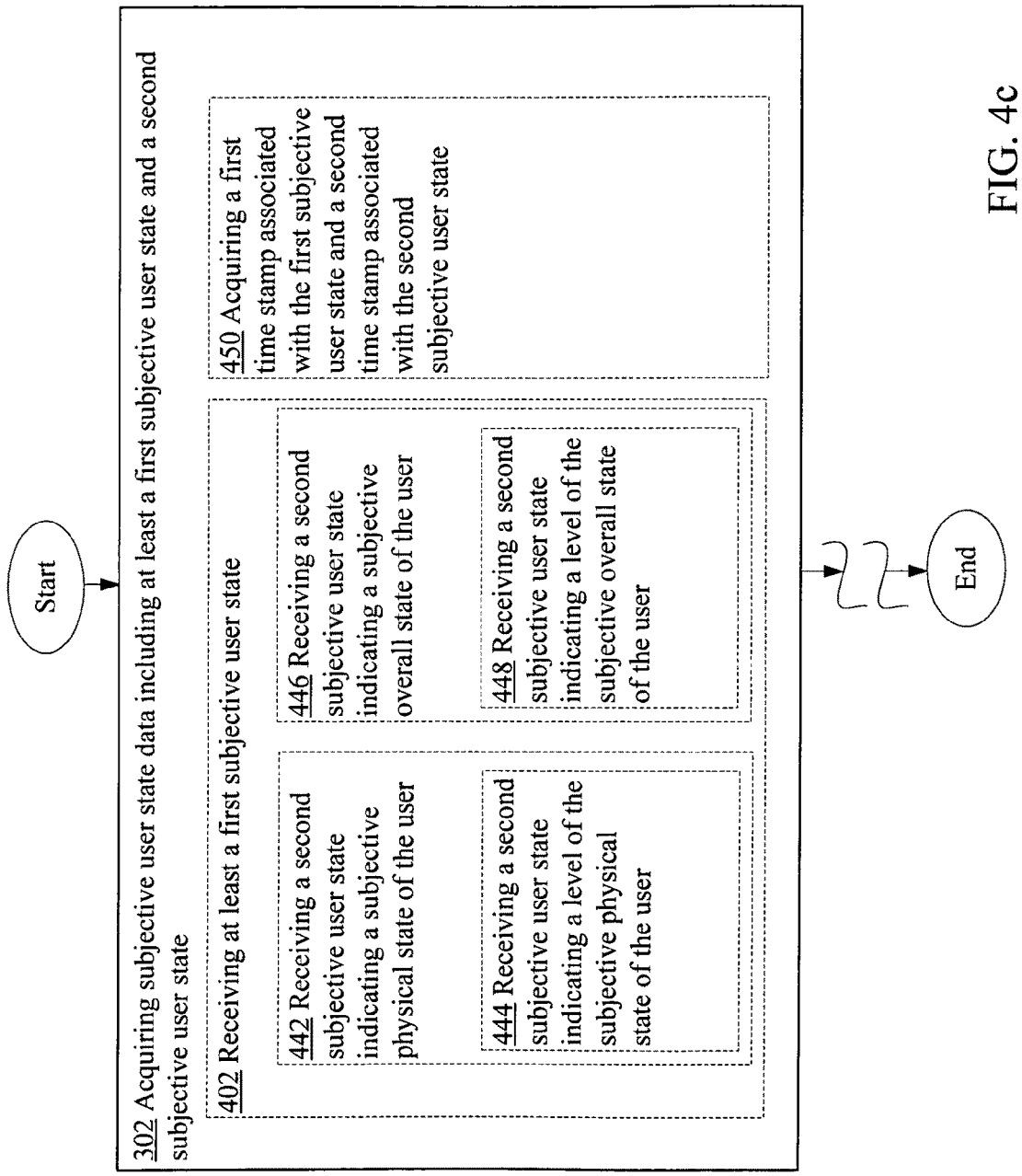
FIG. 4c is a high-level logic flowchart of a process depicting alternate implementations of the subjective user state data acquisition operation 302 of FIG. 3.

In various implementations, the subjective user state data acquisition operation 302 may include one or more additional operations as illustrated in FIGS. 4*a*, 4*b*, 4*c*, and 4*d*. For example, in some implementations the subjective user state data acquisition operation 302 may include a reception operation 402 for receiving at least a first subjective user state as depicted in FIG. 4a to 4c. For instance, the reception module 202 (see FIG. 2a) of the computing device 10 receiving (e.g., via the network interface 120 or via the user interface 122) at least a first subjective user state 60a (e.g., indicating a first subjective mental, physical, or overall state of a user 20*).

In various alternative implementations, the reception operation 402 may further include one or more additional operations. For example, in some implementations, reception operation 402 may include an operation 404 for receiving a first subjective user state from at least one of a wireless network or a wired network as depicted in FIG. 4a. For instance, the reception module 202 (see FIG. 2a) of the computing device 10 receiving (e.g., receiving via the network interface 120) a first subjective user state 60a (e.g., a first subjective overall state of the user 20a indicating, for example, user wellness) from at least one of a wireless network or a wired network 40.

In various implementations, the reception operation 402 may include an operation 406 for receiving a first subjective user state via an electronic message generated by the user as illustrated in FIG. 4a. For instance, the reception module 202 of the computing device 10 receiving (e.g., via a network interface 120) a first subjective user state 60a (e.g., a first subjective mental state of the user 20a indicating, for example, user anger) via an electronic message (e.g., text or audio message) generated by the user 20a.

In some implementations, the reception operation 402 may include an operation 408 for receiving a first subjective user state via a first blog entry generated by the user as depicted in FIG. 4a. For instance, the reception module 202 of the computing device 10 receiving (e.g., via a network interface 120) a first subjective user state 60a (e.g., a first subjective physical state of the user 20a indicating, for example, the presence or absence of pain) via a first blog entry generated by the user 20a.

In some implementations, the reception operation 402 may include an operation 409 for receiving a first subjective user state via a status report generated by the user as depicted in FIG. 4a. For instance, the reception module 202 of the computing device 10 receiving (e.g., through a network interface 120) a first subjective user state via a status report (e.g., a social network status report, a collaborative environment status report, a shared browser status report, or some other status report) generated by the user 20a.

In various implementations, the reception operation 402 may include an operation 410 for receiving a second subjective user state via an electronic message generated by the user as depicted in FIG. 4a. For instance, the reception module 202 of the computing device 10 receiving (e.g., via a network interface 120) a second subjective user state 60b (e.g., a second subjective mental state of the user 20a indicating, for example, user anger) via an electronic message (e.g., text or audio message) generated by the user 20a.

In some implementations, the reception operation 402 may further include an operation 412 for receiving a second subjective user state via a second blog entry generated by the user as depicted in FIG. 4a. For instance, the reception module 202 of the computing device 10 receiving (e.g., via a network interface 120) a second subjective user state (e.g., a second subjective physical state of the user 20a indicating, for example, the presence or absence of pain) via a second blog entry generated by the user 20a.

In some implementations, the reception operation 402 may further include an operation 413 for receiving a second subjective user state via a status report generated by the user as depicted in FIG. 4a. For instance, the reception module 202 of the computing device 10 receiving (e.g., via a network interface 120) a second subjective user state via a status report (e.g., a social network status report, a collaborative environment status report, a shared browser status report, or some other status report) generated by the user 20a.

In various implementations, the reception operation 402 may include an operation 414 for receiving a first subjective user state that was obtained based, at least in part, on data provided by the user, the provided data indicating the first subjective user state associated with the user as depicted in FIG. 4a. For instance, the reception module 202 of the computing device 10 receiving (e.g., via the network interface 120 or via the user interface 122) a first subjective user state (e.g., a first subjective mental, physical, or overall state of the user 20*) that was obtained based, at least in part, on data provided by the user 20*, the provided data indicating the first subjective user state associated with the user 20*.

In some implementations, operation 414 may further include an operation 416 for receiving a first subjective user state that was obtained based, at least in part, on a text entry provided by the user as depicted in FIG. 4a. For instance, the text entry reception module 204 (see FIG. 2a) of the computing device 10 receiving (e.g., via the network interface 120 or the user interface 122) a first subjective user state 60a (e.g., a subjective mental, physical, or overall state of the user 20*) that was obtained based, at least in part, on a text entry provided by the user 20*.

In some implementations, operation 414 may further include an operation 418 for receiving a first subjective user state that was obtained based, at least in part, on an audio entry provided by the user as depicted in FIG. 4a. For instance, the audio entry reception module 206 (see FIG. 2a) of the computing device 10 receiving (e.g., via the network interface 120 or the user interface 122) a first subjective user state 60a (e.g., a subjective mental, physical, or overall state of the user 20*) that was obtained based, at least in part, on an audio entry provided by the user 20*.

In some implementations, operation 414 may further include an operation 419 for receiving a first subjective user state that was obtained based, at least in part, on an image entry provided by the user as depicted in FIG. 4a. For instance, the reception module 202 of the computing device 10 receiving (e.g., via the network interface 120 or via the user interface 122) a first subjective user state 60a that was obtained based, at least in part, on an image entry (e.g., to capture a gesture such a "thumbs up" gesture or to capture a facial expression such as a grimace made by the user 20*) provided by the user 20*.

In various implementations, the reception operation 402 may include an operation 420 for receiving a first subjective user state indicating a subjective mental state of the user as depicted in FIG. 4b. For instance, the reception module 202 of the computing device 10 receiving (e.g., via the network interface 120 or via the user interface 122) a first subjective user state 60a indicating a subjective mental state (e.g., feeling happy or drowsy) of the user 20*.

In some implementations, operation 420 may further include an operation 422 for receiving a first subjective user state indicating a level of the subjective mental state of the user as depicted in FIG. 4a. For instance, the reception module 202 of the computing device 10 receiving (e.g., via the network interface 120 or via the user interface 122) a first subjective user state 60a indicating a level of the subjective mental state (e.g., feeling extremely happy or very drowsy) of the user 20*.

The reception operation 402 in various implementations may include an operation 424 for receiving a first subjective user state indicating a subjective physical state of the user as depicted in FIG. 4b. For instance, the reception module 202 of the computing device 10 receiving (e.g., via the network interface 120 or via the user interface 122) a first subjective user state 60a (e.g., as provided by user 20* via a text or audio entry) indicating a subjective physical state (e.g., absence or presence of a headache or sore back) of the user 20*.

In some implementations, operation 424 may further include an operation 426 for receiving a first subjective user state indicating a level of the subjective physical state of the user as depicted in FIG. 4b. For instance, the reception module 202 of the computing device 10 receiving (e.g., via the network interface 120 or via the user interface 122) a first subjective user state 60a indicating a level of the subjective physical state (e.g., absence or presence of a very bad headache or a very sore back) of the user 20*.

In various implementations, the reception operation 402 may include an operation 428 for receiving a first subjective user state indicating a subjective overall state of the user as depicted in FIG. 4b. For instance, the reception module 202 of the computing device 10 receiving (e.g., via the network interface 120 or via the user interface 122) a first subjective user state 60a indicating a subjective overall state (e.g., user 20* is "well") of the user 20*.

In some implementations, operation 428 may further include an operation 430 for receiving a first subjective user state indicating a level of the subjective overall state of the user as depicted in FIG. 4b. For instance, the reception module 202 of the computing device 10 receiving (e.g., via the network interface 120 or via the user interface 122) a first subjective user state 60a indicating a level of the subjective overall state (e.g., user is "very well") of the user 20*.

In certain implementations, the reception operation 402 may include an operation 432 for receiving a second subjective user state that was obtained based, at least in part, on data provided by the user, the provided data indicating the second subjective user state associated with the user as depicted in FIG. 4b. For instance, the reception module 202 of the computing device 10 receiving (e.g., via the network interface 120 or via the user interface 122) a second subjective user state 60b (e.g., a second subjective mental, physical, or overall state of the user 20*) that was obtained based, at least in part, on data provided by the user 20*, the provided data indicating the second subjective user state associated with the user 20*.

In some implementations, operation 432 may further include an operation 434 for receiving a second subjective user state that was obtained based, at least in part, on a text entry provided by the user as depicted in FIG. 4b. For instance, the text entry reception module 204 (see FIG. 2a) of the computing device 10 receiving (e.g., via the network interface 120 or the user interface 122) a second subjective user state 60b (e.g., a subjective mental, physical, or overall state of the user 20*) that was obtained based, at least in part, on a text entry provided by the user 20*.

In some implementations, operation 432 may further include an operation 436 for receiving a second subjective user state that was obtained based, at least in part, on an audio entry provided by the user as depicted in FIG. 4b. For instance, the audio entry reception module 206 (see FIG. 2a) of the computing device 10 receiving (e.g., via the network interface 120 or the user interface 122) a second subjective user state 60b (e.g., a subjective mental, physical, or overall state of the user 20*) that was obtained based, at least in part, on an audio entry provided by the user 20*.

In some implementations, operation 432 may further include an operation 437 for receiving a second subjective user state that was obtained based, at least in part, on an image entry provided by the user For instance, the reception module 202 of the computing device 10 receiving (e.g., via the network interface 120 or via the user interface 122) a second subjective user state 60b that was obtained based, at least in part, on an image entry (e.g., to capture a gesture such a "thumbs down" gesture or to capture a facial expression such as a smile made by the user 20*) provided by the user 20*.

In various implementations, the reception operation 402 may include an operation 438 for receiving a second subjective user state indicating a subjective mental state of the user as depicted in FIG. 4b. For instance, the reception module 202 of the computing device 10 receiving (e.g., via the network interface 120 or via the user interface 122) a second subjective user state 60b indicating a subjective mental state (e.g., feeling sad or alert) of the user 20*.

In some implementations, operation 438 may further include an operation 440 for receiving a second subjective user state indicating a level of the subjective mental state of the user as depicted in FIG. 4b. For instance, the reception module 202 of the computing device 10 receiving (e.g., via the network interface 120 or via the user interface 122) a second subjective user state 60b indicating a level of the subjective mental state (e.g., feeling extremely sad or extremely alert) of the user 20*.

The reception operation 402, in various implementations, may include an operation 442 for receiving a second subjective user state indicating a subjective physical state of the user as depicted in FIG. 4c. For instance, the reception module 202 of the computing device 10 receiving (e.g., via the network interface 120 or via the user interface 122) a second subjective user state 60b indicating a subjective physical state (e.g., having blurry vision or being nauseous) of the user 20*.

In some implementations, operation 442 may further include an operation 444 for receiving a second subjective user state indicating a level of the subjective physical state of the user as depicted in FIG. 4c. For instance, the reception module 202 of the computing device 10 receiving (e.g., via the network interface 120 or via the user interface 122) a second subjective user state 60b indicating a level of the subjective physical state (e.g., having slightly blurry vision or being slightly nauseous) of the user 20*.

In various implementations, the reception operation 402 may include an operation 446 for receiving a second subjective user state indicating a subjective overall state of the user as depicted in FIG. 4c. For instance, the reception module 202 of the computing device 10 receiving (e.g., via the network interface 120 or via the user interface 122) a second subjective user state 60b indicating a subjective overall state (e.g., user 20* is "exhausted") of the user 20*.

In some implementations, operation 446 may further include an operation 448 for receiving a second subjective user state indicating a level of the subjective overall state of the user as depicted in FIG. 4c. For instance, the reception module 202 of the computing device 10 receiving (e.g., via the network interface 120 or via the user interface 122) a second subjective user state 60b indicating a level of the subjective overall state (e.g., user 20* is "extremely exhausted") of the user 20*.

In various implementations, the subjective user state data acquisition operation 302 may include an operation 450 for acquiring a first time stamp associated with the first subjective user state and a second time stamp associated with the second subjective user state as depicted in FIG. 4c. For instance, the subjective user state data acquisition module 102 of the computing device 10 acquiring (e.g., receiving via the network interface 120 or generating via time stamp module 124) a first time stamp associated with the first subjective user state 60a and a second time stamp associated with the second subjective user state 60b.

Figure 4D:
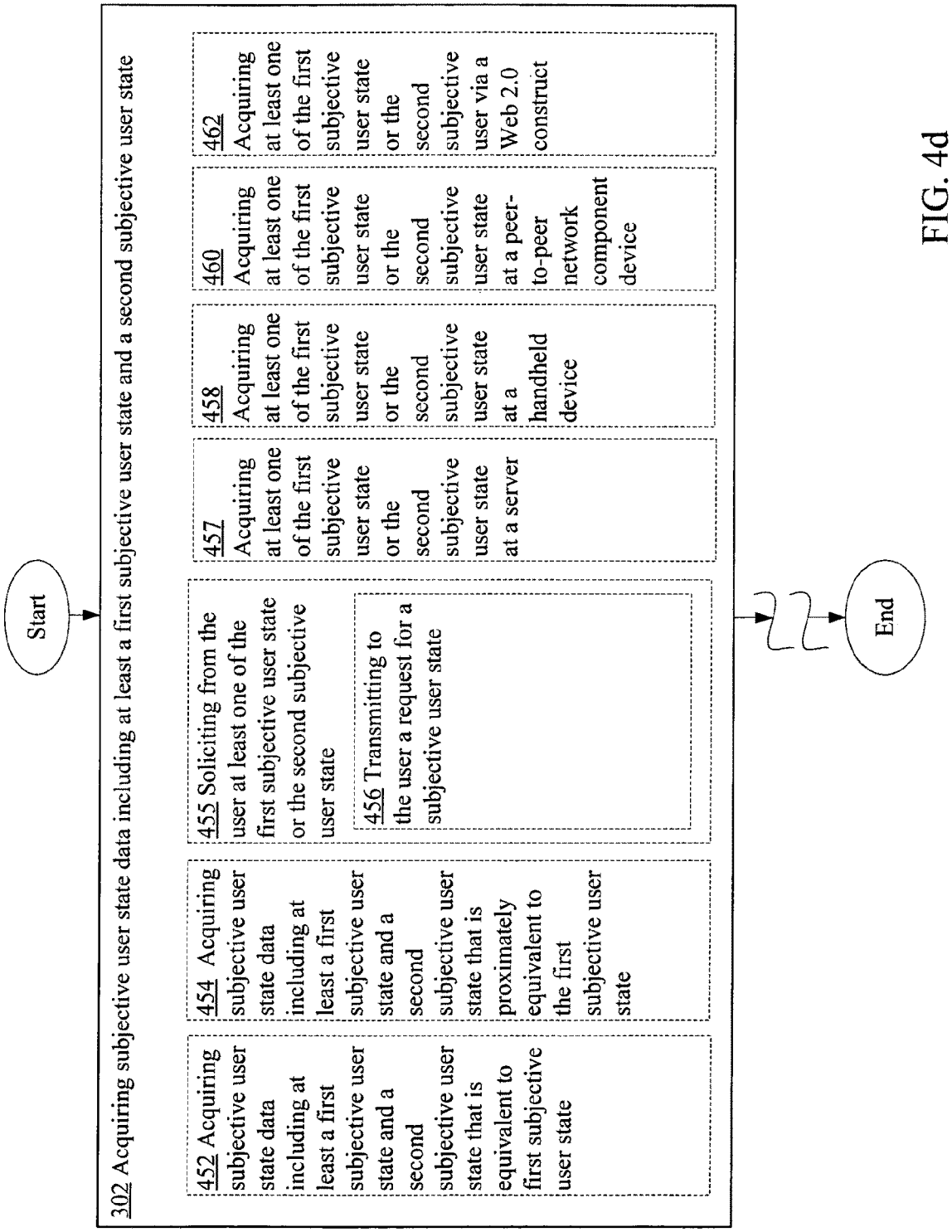
FIG. 4d is a high-level logic flowchart of a process depicting alternate implementations of the subjective user state data acquisition operation 302 of FIG. 3.

In various implementations, the subjective user state data acquisition operation 302 may include an operation 452 for acquiring subjective user state data including at least a first subjective user state and a second subjective user state that is equivalent to the first subjective user state as depicted in FIG. 4d. For instance, the subjective user state data acquisition module 102 acquiring (e.g., via network interface 120 or via user interface 122) subjective user state data 60 including at least a first subjective user state (e.g., user 20\* feels sleepy) and a second subjective user state (e.g., user 20\* feels sleepy) that is equivalent to the first subjective user state 60a.

In various implementations, the subjective user state data acquisition operation 302 may include an operation 454 for acquiring subjective user state data including at least a first subjective user state and a second subjective user state that is proximately equivalent to the first subjective user state as depicted in FIG. 4d. For instance, the subjective user state data acquisition module 102 acquiring (e.g., via network interface 120 or via user interface 122) subjective user state data 60 including at least a first subjective user state 60a (e.g., user 20\* feels angry) and a second subjective user state 60b (e.g., user 20\* feels extremely angry) that is proximately equivalent to the first subjective user state 60a.

In various implementations, the subjective user state data acquisition operation 302 may include an operation 455 for soliciting from the user at least one of the first subjective user state or the second subjective user state as depicted in FIG. 4d. For instance, the solicitation module 206 (see FIG. 2a) of the computing device 10 soliciting from the user 20\* (e.g., via network interface 120 or via user interface 122) at least one of the first subjective user state 60a (e.g., mental, physical, or overall user state) or the second subjective user state 60b (e.g., mental, physical, or overall user state).

In some implementations, operation 455 may further include an operation 456 for transmitting to the user a request for a subjective user state as depicted in FIG. 4d. For instance, the transmission module 207 (see FIG. 2a) of the computing device 10 transmitting (e.g., via the network interface 120) to the user 20a a request for a subjective user state. In some cases, the request may provide to the user 20a an option to make a section from a number of alternatives subjective user states (e.g., are you happy, very happy, sad, or very sad?).

In various implementations, the subjective user state data acquisition operation 302 may include an operation 457 for acquiring at least one of the first subjective user state or the second subjective user state at a server as depicted in FIG. 4d. For instance, the subjective user state data acquisition module 102 of the computing device 10 acquiring at least one of the first subjective user state 60a (e.g., user is "sleepy") or the second subjective user state 60b (e.g., user is again "sleepy") at a server (e.g., computing device 10 being a network server).

In various implementations, the subjective user state data acquisition operation 302 may include an operation 458 for acquiring at least one of the first subjective user state or the second subjective user state at a handheld device as depicted in FIG. 4d. For instance, the subjective user state data acquisition module 102 of the computing device 10 acquiring at least one of the first subjective user state 60a (e.g., user is "dizzy") or the second subjective user state 60b (e.g., user is again "dizzy") at a handheld device (e.g., computing device 10 being a mobile phone or a PDA).

In various implementations, the subjective user state data acquisition operation 302 may include an operation 460 for acquiring at least one of the first subjective user state or the second subjective user state at a peer-to-peer network component device as depicted in FIG. 4d. For instance, the subjective user state data acquisition module 102 of the computing device 10 acquiring at least one of the first subjective user state 60a (e.g., user feels "alert") or the second subjective user state 60b (e.g., user again feels "alert") at a peer-to-peer network component device (e.g., computing device 10).

In various implementations, the subjective user state data acquisition operation 302 may include an operation 462 for acquiring at least one of the first subjective user state or the second subjective user via a Web 2.0 construct as depicted in FIG. 4d. For instance, the subjective user state data acquisition module 102 of the computing device 10 acquiring at least one of the first subjective user state 60a (e.g., user feels ill) or the second subjective user 60b (e.g., user again feels ill) via a Web 2.0 construct.

Figure 4E:
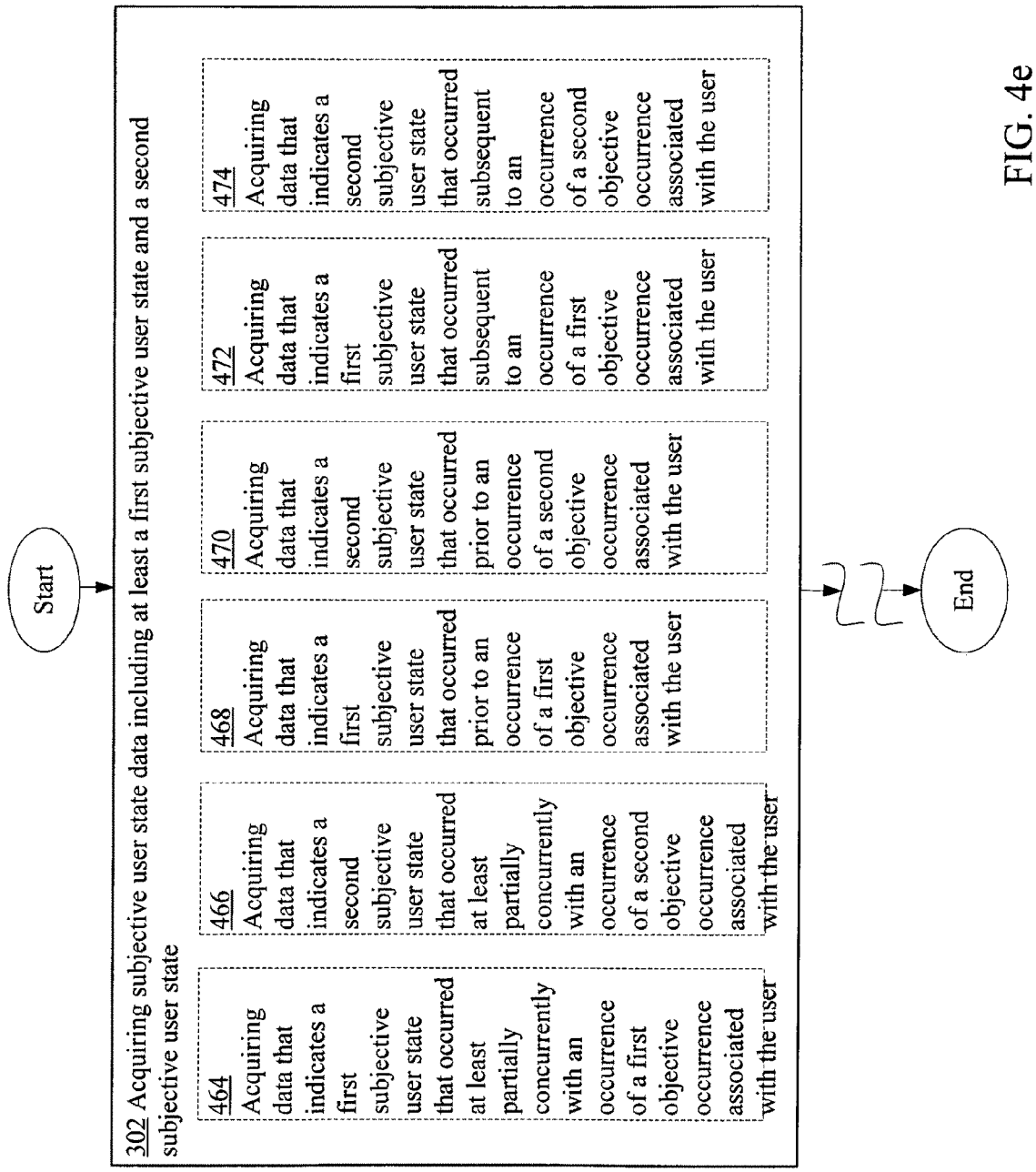
FIG. 4e is a high-level logic flowchart of a process depicting alternate implementations of the subjective user state data acquisition operation 302 of FIG. 3.

In some implementations, the subjective user state data acquisition operation 302 may include an operation 464 for acquiring data that indicates a first subjective user state that occurred at least partially concurrently with an occurrence of a first objective occurrence associated with the user as depicted in FIG. 4e. For instance, the subjective user state data acquisition module 102 of the computing device 10 acquiring (e.g., via network interface 120 or via user interface 122) data that indicates a first subjective user state that occurred at least partially concurrently with an occurrence of a first objective occurrence associated with the user 20\*.

In some implementations, the subjective user state data acquisition operation 302 may include an operation 466 for acquiring data that indicates a second subjective user state that occurred at least partially concurrently with an occurrence of a second objective occurrence associated with the user as depicted in FIG. 4e. For instance, the subjective user state data acquisition module 102 of the computing device 10 acquiring (e.g., via network interface 120 or via user interface 122) data that indicates a second subjective user state that occurred at least partially concurrently with an occurrence of a second objective occurrence associated with the user 20\*.

In some implementations, the subjective user state data acquisition operation 302 may include an operation 468 for acquiring data that indicates a first subjective user state that occurred prior to an occurrence of a first objective occurrence associated with the user as depicted in FIG. 4e. For instance, the subjective user state data acquisition module 102 of the computing device 10 acquiring (e.g., via network interface 120 or via user interface 122) data that indicates a first subjective user state that occurred prior to an occurrence of a first objective occurrence associated with the user 20\* (e.g., first subjective user state occurred within a predefined time increment before the occurrence of the first objective occurrence such as occurring within 15 minutes, 30 minutes, 1 hour, 1 day, or some other time increment before the occurrence of the first objective occurrence).

In some implementations, the subjective user state data acquisition operation 302 may include an operation 470 for acquiring data that indicates a second subjective user state that occurred prior to an occurrence of a second objective occurrence associated with the user as depicted in FIG. 4e. For instance, the subjective user state data acquisition module 102 of the computing device 10 acquiring (e.g., via network interface 120 or via user interface 122) data that indicates a second subjective user state that occurred prior to an occurrence of a second objective occurrence associated with the user 20\* (e.g., second subjective user state occurred within a predefined time increment before the occurrence of the second objective occurrence such as occurring within 15 minutes, 30 minutes, 1 hour, 1 day, or some other predefined time increment before the occurrence of the second objective occurrence).

In some implementations, the subjective user state data acquisition operation 302 may include an operation 472 for acquiring data that indicates a first subjective user state that occurred subsequent to an occurrence of a first objective occurrence associated with the user as depicted in FIG. 4e. For instance, the subjective user state data acquisition module 102 of the computing device 10 acquiring (e.g., via network interface 120 or via user interface 122) data that indicates a first subjective user state that occurred subsequent to an occurrence of a first objective occurrence associated with the user 20* (e.g., first subjective user state occurred within a predefined time increment after the occurrence of the first objective occurrence such as occurring within 15 minutes, 30 minutes, 1 hour, 1 day, or some other predefined time increment after the occurrence of the first objective occurrence).

In some implementations, the subjective user state data acquisition operation 302 may include an operation 474 for acquiring data that indicates a second subjective user state that occurred subsequent to an occurrence of a second objective occurrence associated with the user as depicted in FIG. 4e. For instance, the subjective user state data acquisition module 102 of the computing device 10 acquiring (e.g., via network interface 120 or via user interface 122) data that indicates a second subjective user state that occurred subsequent to an occurrence of a second objective occurrence associated with the user 20* (e.g., second subjective user state occurred within a predefined time increment after the occurrence of the second objective occurrence such as occurring within 15 minutes, 30 minutes, 1 hour, 1 day, or some other time increment after the occurrence of the second objective occurrence).

Figure 5A:
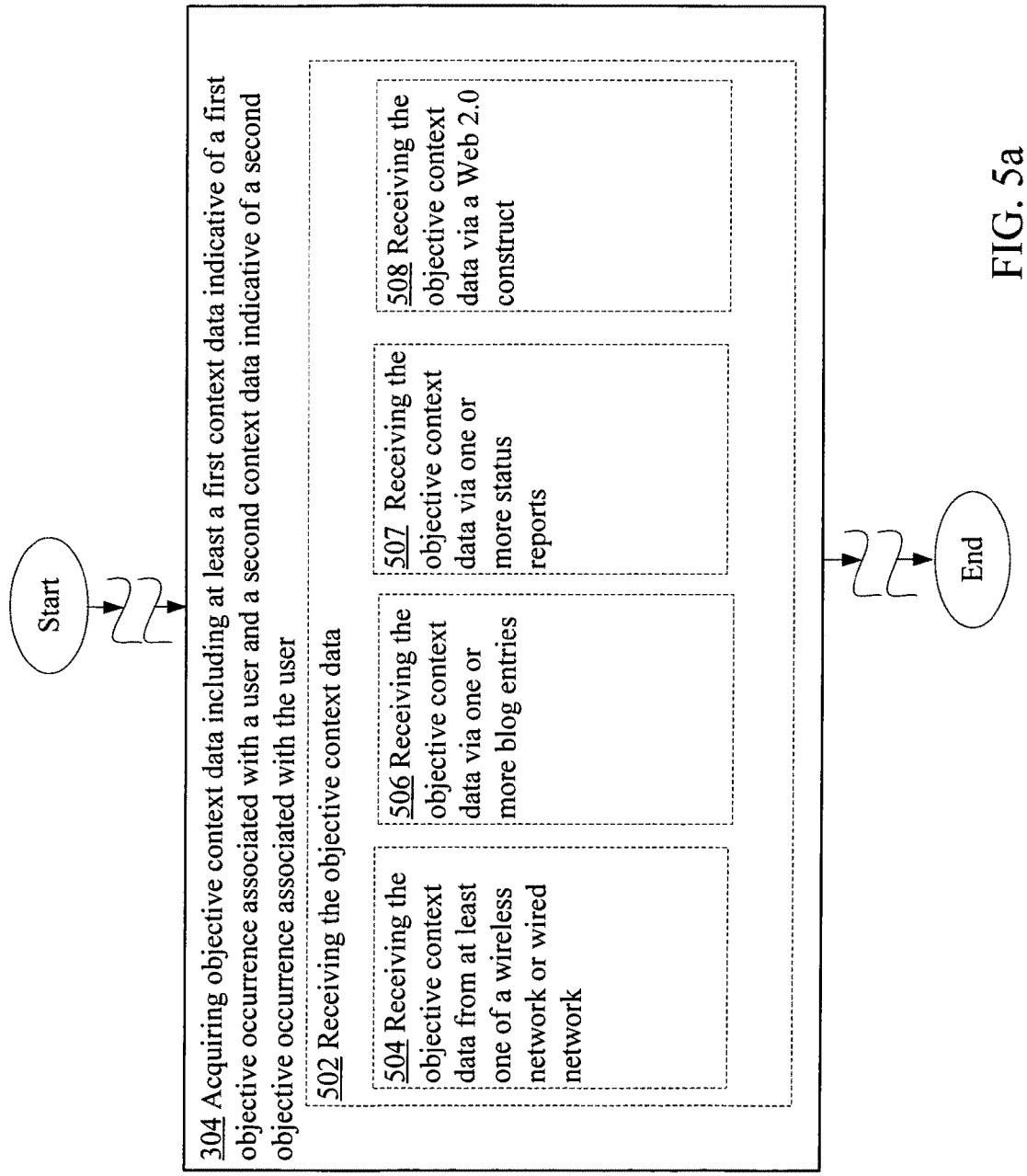
FIG. 5a is a high-level logic flowchart of a process depicting alternate implementations of the objective context data acquisition operation 304 of FIG. 3.

Referring back to FIG. 3, in various implementations the objective context data acquisition operation 304 may include one or more additional operations as illustrated in FIGS. 5a, 5b, 5c, 5d, and 5e. For example, in some implementations, the objective context data acquisition operation 304 may include a reception operation 502 for receiving the objective context data as depicted in FIG. 5a. For instance, the objective context data reception module 208 of the computing device 10 receiving (e.g., via a network interface 120 or via a user interface 122) the objective context data 70a, 70b, or 70c.

In some implementations, the reception operation 502 may further include one or more additional operations. For example, in some implementations, the reception operation 502 may include an operation 504 for receiving the objective context data from at least one of a wireless network or wired network as depicted in FIG. 5a. For instance, the objective context data reception module 208 of the computing device 10 receiving (e.g., via network interface 120) the objective context data 70a, 70b, or 70c from at least one of a wireless network or wired network 40.

In some implementations, the reception operation 502 may include an operation 506 for receiving the objective context data via one or more blog entries as depicted in FIG. 5a. For instance, the objective context data reception module 208 of the computing device 10 receiving (e.g., via network interface 120) the objective context data 70a or 70c via one or more blog entries (e.g., microblog entries).

In some implementations, the reception operation 502 may include an operation 507 for receiving the objective context data via one or more status reports as depicted in FIG. 5a. For instance, the objective context data reception module 208 of the computing device 10 receiving (e.g., via network interface 120) the objective context data 70a or 70c via one or more status reports (e.g., social network status reports).

In some implementations, the reception operation 502 may include an operation 508 for receiving the objective context data via a Web 2.0 construct as depicted in FIG. 5a. For instance, the objective context data reception module 208 of the computing device 10 receiving (e.g., via network interface 120) the objective context data 70a, 70b, or 70c via a Web 2.0 construct (e.g., web 2.0 application 230).

Figure 5B:
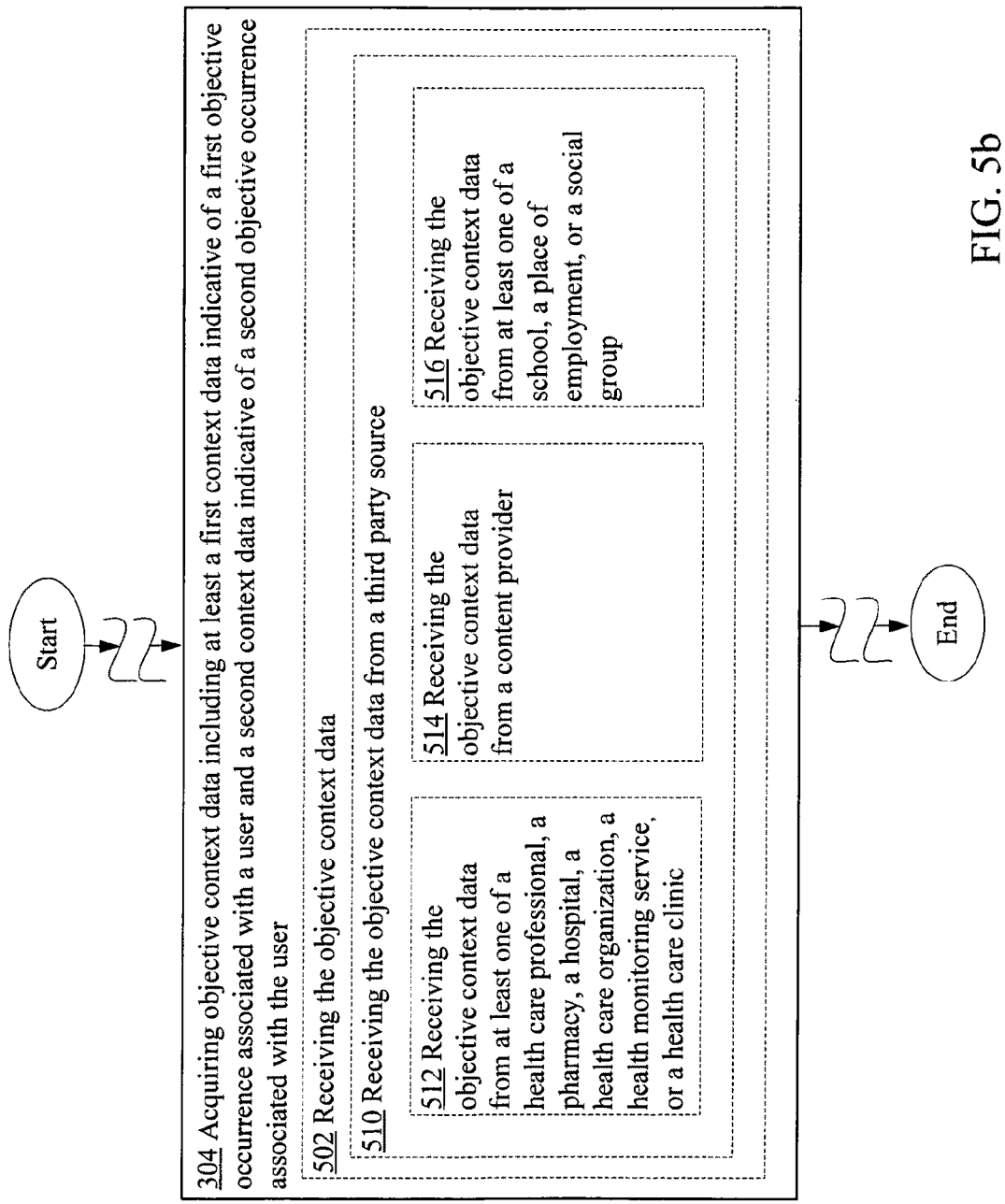
FIG. 5b is a high-level logic flowchart of a process depicting alternate implementations of the objective context data acquisition operation 304 of FIG. 3.

In various implementations, the reception operation 502 may include an operation 510 for receiving the objective context data from one or more third party sources as depicted in FIG. 5b. For instance, the objective context data reception module 208 of the computing device 10 receiving (e.g., via network interface 120) the objective context data 70a from one or more third party sources 50.

In some implementations, operation 510 may further include an operation 512 for receiving the objective context data from at least one of a health care professional, a pharmacy, a hospital, a health care organization, a health monitoring service, or a health care clinic as depicted in FIG. 5b. For instance, the objective context data reception module 208 of the computing device 10 receiving (e.g., via network interface 120) the objective context data 70a from at least one of a health care professional, a pharmacy, a hospital, a health care organization, a health monitoring service, or a health care clinic.

In some implementations, operation 510 may further include an operation 514 for receiving the objective context data from a content provider as depicted in FIG. 5b. For instance, the objective context data reception module 208 of the computing device 10 receiving (e.g., via network interface 120) the objective context data 70a from a content provider.

In some implementations, operation 510 may further include an operation 516 for receiving the objective context data from at least one of a school, a place of employment, or a social group as depicted in FIG. 5b. For instance, the objective context data reception module 208 of the computing device 10 receiving (e.g., via network interface 120) the objective context data 70a from at least one of a school, a place of employment, or a social group.

Figure 5C:
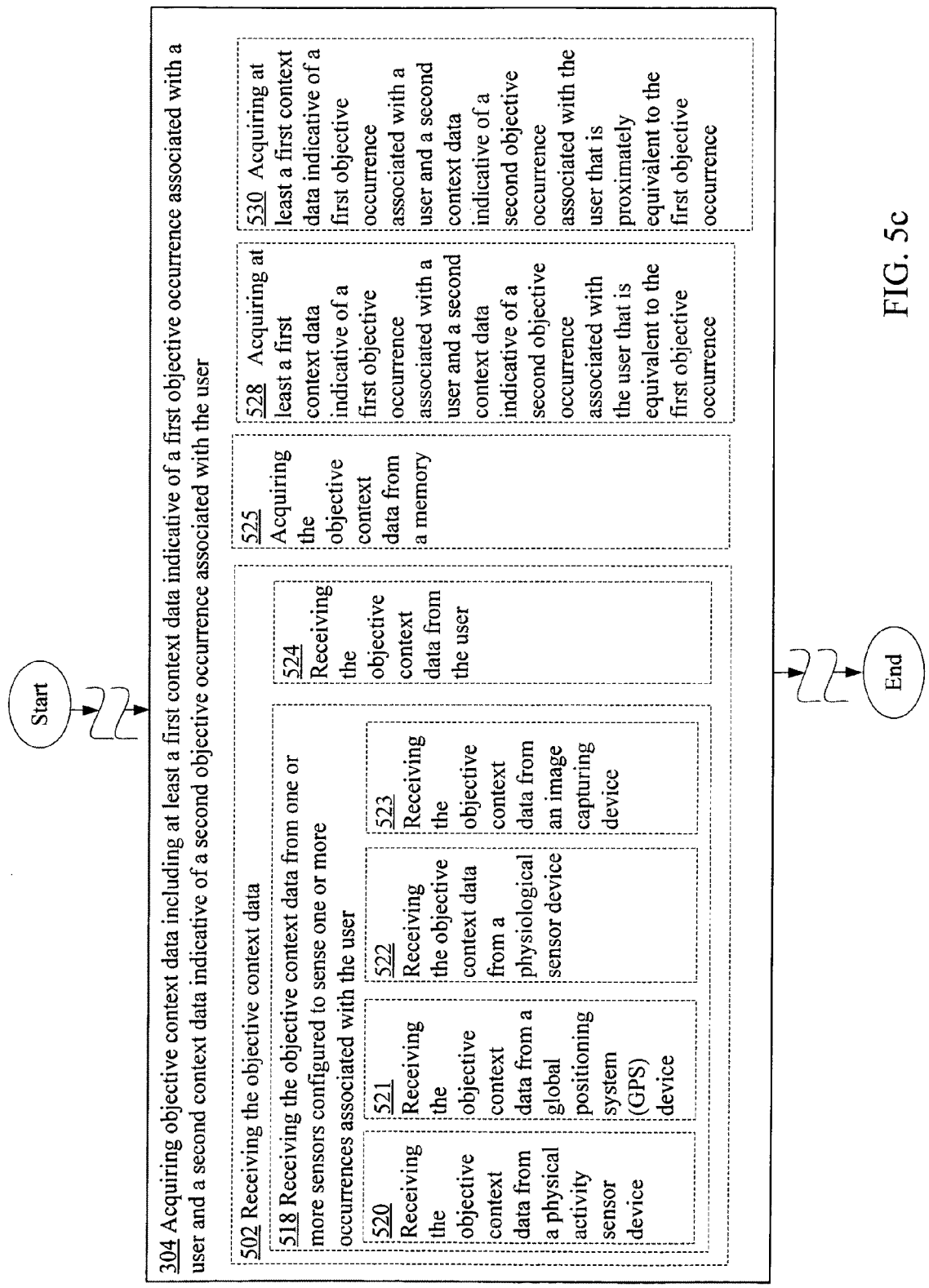
FIG. 5c is a high-level logic flowchart of a process depicting alternate implementations of the objective context data acquisition operation 304 of FIG. 3.

In various implementations, the reception operation 502 may include an operation 518 for receiving the objective context data from one or more sensors configured to sense one or more objective occurrences associated with the user as depicted in FIG. 5c. For instance, the objective context data reception module 208 of the computing device 10 receiving (e.g., via network interface 120) the objective context data 70b from one or more sensors 35 configured to sense one or more objective occurrences (e.g., blood pressure, blood sugar level, location of the user 20a, and so forth) associated with the user 20a.

In some implementations, operation 518 may further include an operation 520 for receiving the objective context data from a physical activity sensor device as depicted in FIG. 5c. For instance, the objective context data reception module 208 of the computing device 10 receiving (e.g., via network interface 120) the objective context data 70b from a physical activity sensor device (e.g., a pedometer or a sensor on an exercise machine).

In some implementations, operation 518 may further include an operation 521 for receiving the objective context data from a global positioning system (GPS) device as depicted in FIG. 5c. For instance, the objective context data reception module 208 of the computing device 10 receiving (e.g., via network interface 120) the objective context data 70*b* from a global positioning system (GPS) device (e.g., mobile device 30).

In some implementations, operation 518 may further include an operation 522 for receiving the objective context data from a physiological sensor device as depicted in FIG. 5*c*. For instance, the objective context data reception module 208 of the computing device 10 receiving (e.g., via network interface 120) the objective context data 70*b* from a physiological sensor device (e.g., blood pressure monitor, heart rate monitor, glucometer, and so forth).

In some implementations, operation 518 may further include an operation 523 for receiving the objective context data from an image capturing device as depicted in FIG. 5*c*. For instance, the objective context data reception module 208 of the computing device 10 receiving (e.g., via network interface 120) the objective context data 70*b* from an image capturing device (e.g., video or digital camera).

In various implementations, the reception operation 502 may include an operation 524 for receiving the objective context data from the user as depicted in FIG. 5*c*. For instance, the objective context data reception module 208 of the computing device 10 receiving (e.g., via network interface 120 or via user interface 122) the objective context data 70*c* from the user 20\*.

In various implementations, the objective context data acquisition operation 304 of FIG. 3 may include an operation 525 for acquiring the objective context data from a memory as depicted in FIG. 5*c*. For instance, the objective context data acquisition module 104 of the computing device 10 acquiring the objective context data 70*d* (e.g., tidal chart or moon phase chart) from memory 140.

In various implementations, the objective context data acquisition operation 304 may include an operation 528 for acquiring at least a first context data indicative of a first objective occurrence associated with a user and a second context data indicative of a second objective occurrence associated with the user that is equivalent to the first objective occurrence as depicted in FIG. 5*c*. For instance, the objective context data acquisition module 104 of the computing device 10 acquiring at least a first context data indicative of a first objective occurrence (e.g., cloudy weather) associated with a user 20\* and a second context data indicative of a second objective occurrence (e.g., cloudy weather) associated with the user 20\* that is equivalent to the first objective occurrence.

In various implementations, the objective context data acquisition operation 304 may include an operation 530 for acquiring at least a first context data indicative of a first objective occurrence associated with a user and a second context data indicative of a second objective occurrence associated with the user that is proximately equivalent to the first objective occurrence as depicted in FIG. 5*c*. For instance, the objective context data acquisition module 104 of the computing device 10 acquiring at least a first context data indicative of a first objective occurrence (e.g., drank 8 cans of beer) associated with a user 20\* and a second context data indicative of a second objective occurrence (e.g., drank 7 cans of beer) associated with the user 20\* that is proximately equivalent to the first objective occurrence.

Figure 5D:
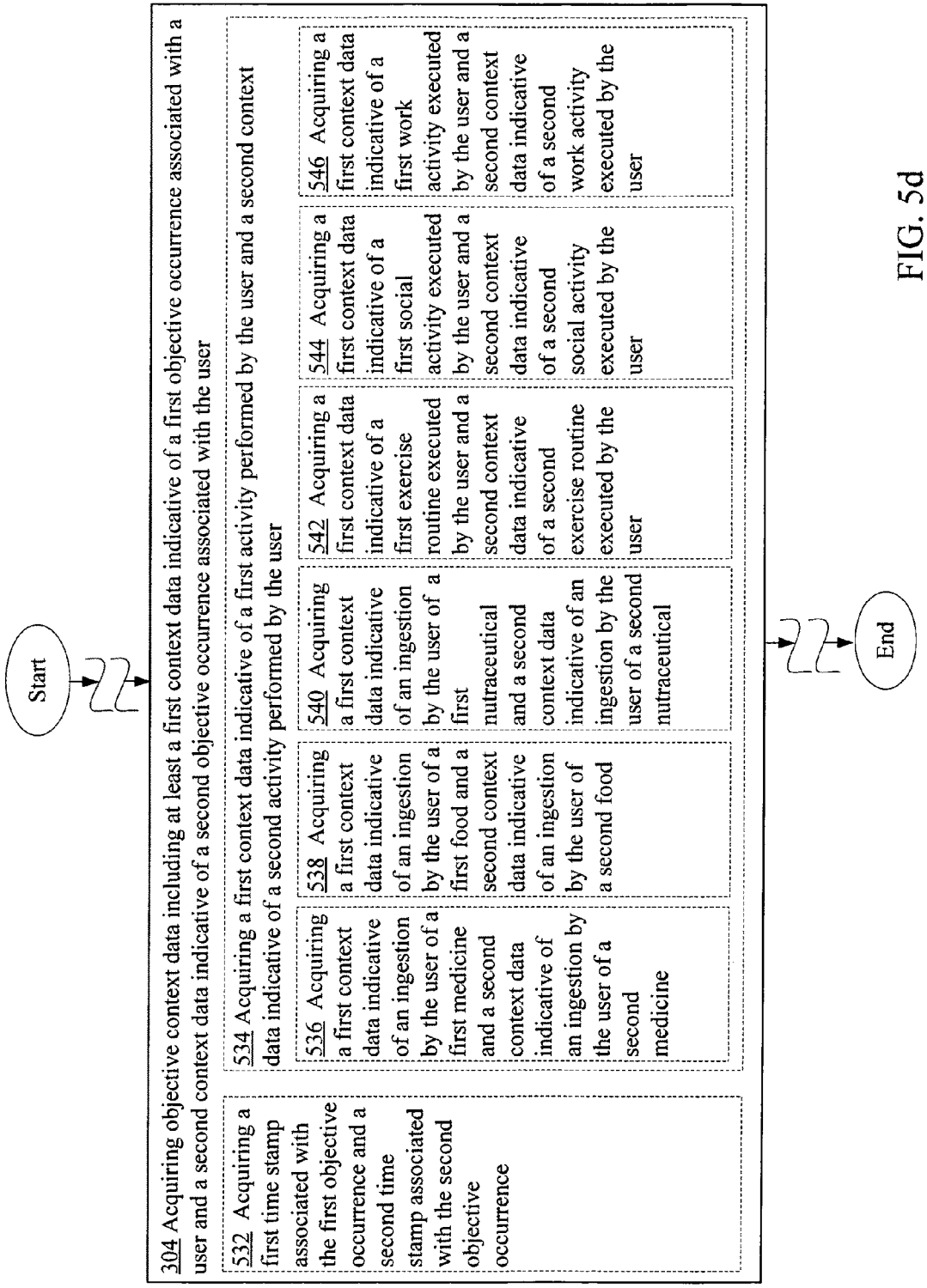
FIG. 5d is a high-level logic flowchart of a process depicting alternate implementations of the objective context data acquisition operation 304 of FIG. 3.

In various implementations, the objective context data acquisition operation 304 may include an operation 532 for acquiring a first time stamp associated with the first objective occurrence and a second time stamp associated with the second objective occurrence as depicted in FIG. 5*d*. For instance, the objective context data acquisition module 104 of the computing device 10 acquiring (e.g., receiving via network interface 120 or generating via time stamp module 124) a first time stamp associated with the first objective occurrence (e.g., jogged for 40 minutes) and a second time stamp associated with the second objective occurrence (e.g., jogged for 38 minutes).

In various implementations, the objective context data acquisition operation 304 may include an operation 534 for acquiring a first context data indicative of a first activity performed by the user and a second context data indicative of a second activity performed by the user as depicted in FIG. 5*d*. For instance, the objective context data acquisition module 104 of the computing device 10 acquiring (e.g., via network interface 120 or via user interface 122) a first context data indicative of a first activity (e.g., ingesting a particular food, medicine, or nutraceutical) performed by the user and a second context data indicative of a second activity (e.g., ingesting the same or similar particular food, medicine, or nutraceutical) performed by the user 20\*.

In some implementations, operation 534 may also include an operation 536 for acquiring a first context data indicative of an ingestion by the user of a first medicine and a second context data indicative of an ingestion by the user of a second medicine as depicted in FIG. 5*d*. For instance, the objective context data acquisition module 104 of the computing device 10 acquiring (e.g., via network interface 120 or via user interface 122) a first context data indicative of an ingestion by the user 20\* of a first medicine (e.g., 600 mg dose of ibuprofen) and a second context data indicative of an ingestion by the user of a second medicine e.g., another 600 mg dose of ibuprofen).

In some implementations, operation 534 may also include an operation 538 for acquiring a first context data indicative of an ingestion by the user of a first food and a second context data indicative of an ingestion by the user of a second food as depicted in FIG. 5*d*. For instance, the objective context data acquisition module 104 of the computing device 10 acquiring (e.g., via network interface 120 or via user interface 122) a first context data indicative of an ingestion by the user 20\* of a first food (e.g., 16 ounces of orange juice) and a second context data indicative of an ingestion by the user 20\* of a second food (e.g., another 16 ounces of orange juice).

In some implementations, operation 534 may also include an operation 540 for acquiring a first context data indicative of an ingestion by the user of a first nutraceutical and a second context data indicative of an ingestion by the user of a second nutraceutical as depicted in FIG. 5*d*. For instance, the objective context data acquisition module 104 of the computing device 10 acquiring (e.g., via network interface 120 or via user interface 122) a first context data indicative of an ingestion by the user 20\* of a first nutraceutical (e.g., a serving of ginkgo biloba) and a second context data indicative of an ingestion by the user 20\* of a second nutraceutical (e.g., a serving of ginkgo biloba).

In some implementations, operation 534 may also include an operation 542 for acquiring a first context data indicative of a first exercise routine executed by the user and a second context data indicative of a second exercise routine executed by the user as depicted in FIG. 5*d*. For instance, the objective context data acquisition module 104 of the computing device 10 acquiring (e.g., via network interface 120 or via user interface 122) a first context data indicative of a first exercise routine (e.g., exercising 30 minutes on a treadmill machine) executed by the user 20\* and a second context data indicative of a second exercise routine (e.g., exercising another 30 minutes on the treadmill machine) executed by the user 20\*.

In some implementations, operation 534 may also include an operation 544 for acquiring a first context data indicative of a first social activity executed by the user and a second context data indicative of a second social activity executed by the user as depicted in FIG. 5d. For instance, the objective context data acquisition module 104 of the computing device 10 acquiring (e.g., via network interface 120 or via user interface 122) a first context data indicative of a first social activity (e.g., going out on a blind date) executed by the user 20* and a second context data indicative of a second social activity (e.g., going out again on a blind date) executed by the user 20*.

In some implementations, operation 534 may also include an operation 546 for acquiring a first context data indicative of a first work activity executed by the user and a second context data indicative of a second work activity executed by the user as depicted in FIG. 5d. For instance, the objective context data acquisition module 104 of the computing device 10 acquiring (e.g., via network interface 120 or via user interface 122) a first context data indicative of a first work activity (e.g., two hours of overtime work) executed by the user 20* and a second context data indicative of a second work activity (e.g., another two hours of overtime work) executed by the user 20*.

Figure 5E:
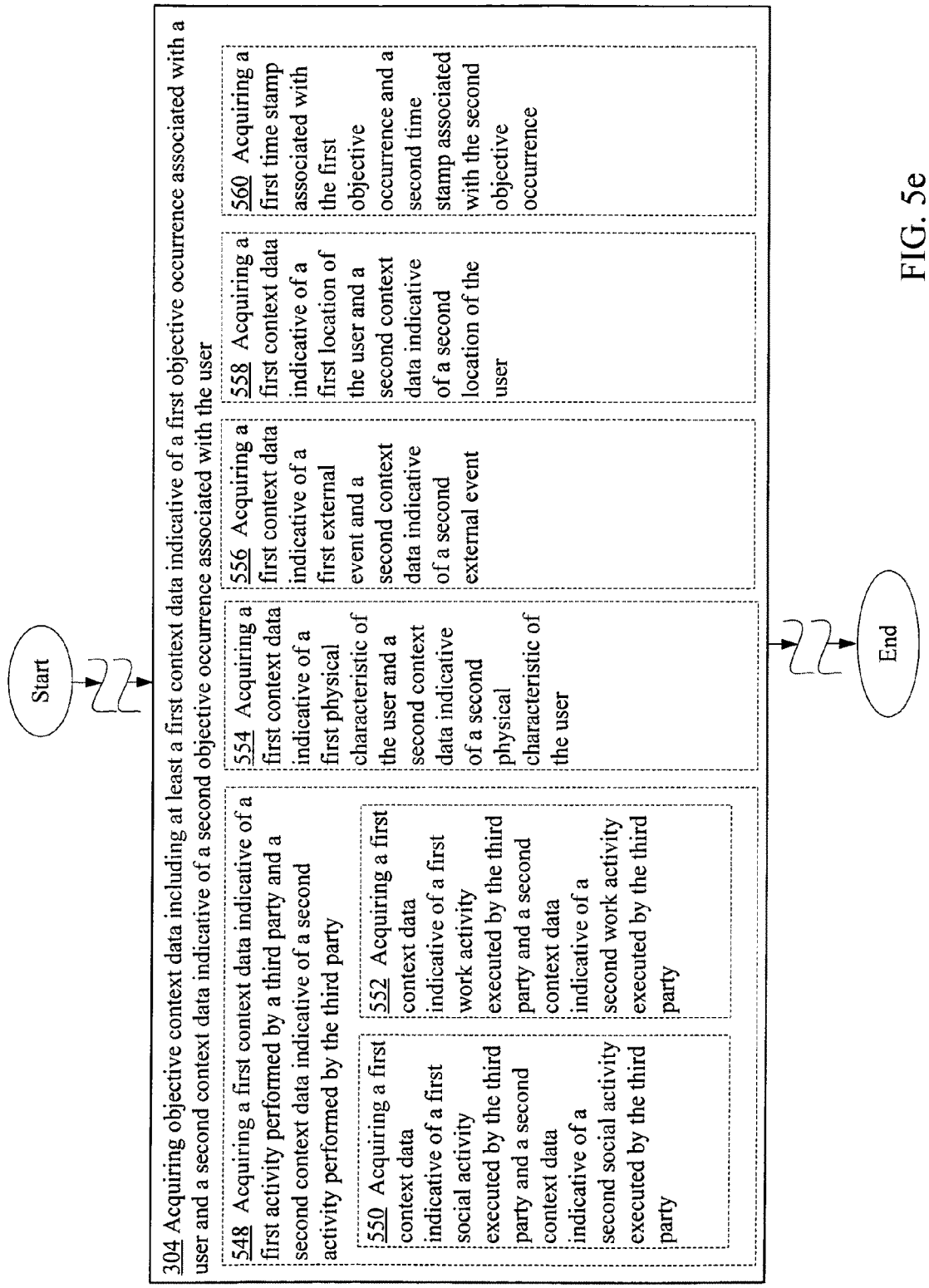
FIG. 5e is a high-level logic flowchart of a process depicting alternate implementations of the objective context data acquisition operation 304 of FIG. 3.

In various implementations, the objective context data acquisition operation 304 of FIG. 3 may include an operation 548 for acquiring a first context data indicative of a first activity performed by a third party and a second context data indicative of a second activity performed by the third party as depicted in FIG. 5e. For instance, the objective context data acquisition module 104 of the computing device 10 acquiring (e.g., via network interface 120 or via user interface 122) a first context data indicative of a first activity performed by a third party (e.g., dental procedure performed by a dentist on the user 20* as reported by the dentist or by the user 20*) and a second context data indicative of a second activity performed by the third party (e.g., another dental procedure performed by a dentist on the user 20* as reported by the dentist or by the user 20*).

In some implementations, operation 548 may further include an operation 550 for acquiring a first context data indicative of a first social activity executed by the third party and a second context data indicative of a second social activity executed by the third party as depicted in FIG. 5e. For instance, the objective context data acquisition module 104 of the computing device 10 acquiring (e.g., via network interface 120 or via user interface 122) a first context data indicative of a first social activity executed by the third party (e.g., spouse going away to visit a relative) and a second context data indicative of a second social activity executed by the third party (e.g., spouse going away again to visit a relative).

In some implementations, operation 548 may further include an operation 552 for acquiring a first context data indicative of a first work activity executed by the third party and a second context data indicative of a second work activity executed by the third party as depicted in FIG. 5e. For instance, the objective context data acquisition module 104 of the computing device 10 acquiring (e.g., via network interface 120 or via user interface 122) a first context data indicative of a first work activity executed by the third party (e.g., boss meeting with the user 20*) and a second context data indicative of a second work activity executed by the third party (e.g., boss meeting with the user 20*).

In various implementations, the objective context data acquisition operation 304 of FIG. 3 may include an operation 554 for acquiring a first context data indicative of a first physical characteristic of the user and a second context data indicative of a second physical characteristic of the user as depicted in FIG. 5e. For instance, the objective context data acquisition module 104 of the computing device 10 acquiring (e.g., via network interface 120 or via user interface 122) a first context data indicative of a first physical characteristic of the user 20* (e.g., high blood sugar level) and a second context data indicative of a second physical characteristic of the user 20* (e.g., another high blood sugar level).

In various implementations, the objective context data acquisition operation 304 may include an operation 556 for acquiring a first context data indicative of a first external event and a second context data indicative of a second external event as depicted in FIG. 5e. For instance, the objective context data acquisition module 104 of the computing device 10 acquiring (e.g., via network interface 120 or via user interface 122) a first context data indicative of a first external event (e.g., stock market drops 500 points) and a second context data indicative of a second external event (e.g., stock market again drops 500 points).

In various implementations, the objective context data acquisition operation 304 may include an operation 558 for acquiring a first context data indicative of a first location of the user and a second context data indicative of a second location of the user as depicted in FIG. 5e. For instance, the objective context data acquisition module 104 of the computing device 10 acquiring (e.g., via network interface 120 or via user interface 122) a first context data indicative of a first location (e.g., Hawaii) of the user 20* (e.g., during a first point in time) and a second context data indicative of a second location (e.g., Hawaii) of the user 20* (e.g., during second point in time).

In various implementations, the objective context data acquisition operation 304 may include an operation 560 for acquiring a first time stamp associated with the first objective occurrence and a second time stamp associated with the second objective occurrence as depicted in FIG. 5e. For instance, the objective context data acquisition module 104 of the computing device 10 acquiring (e.g., via network interface 120 or via time stamp module 124) a first time stamp associated with the first objective occurrence (e.g., consumption of medicine) and a second time stamp associated with the second objective occurrence (e.g., consumption again of the same or similar medicine).

Figure 6A:
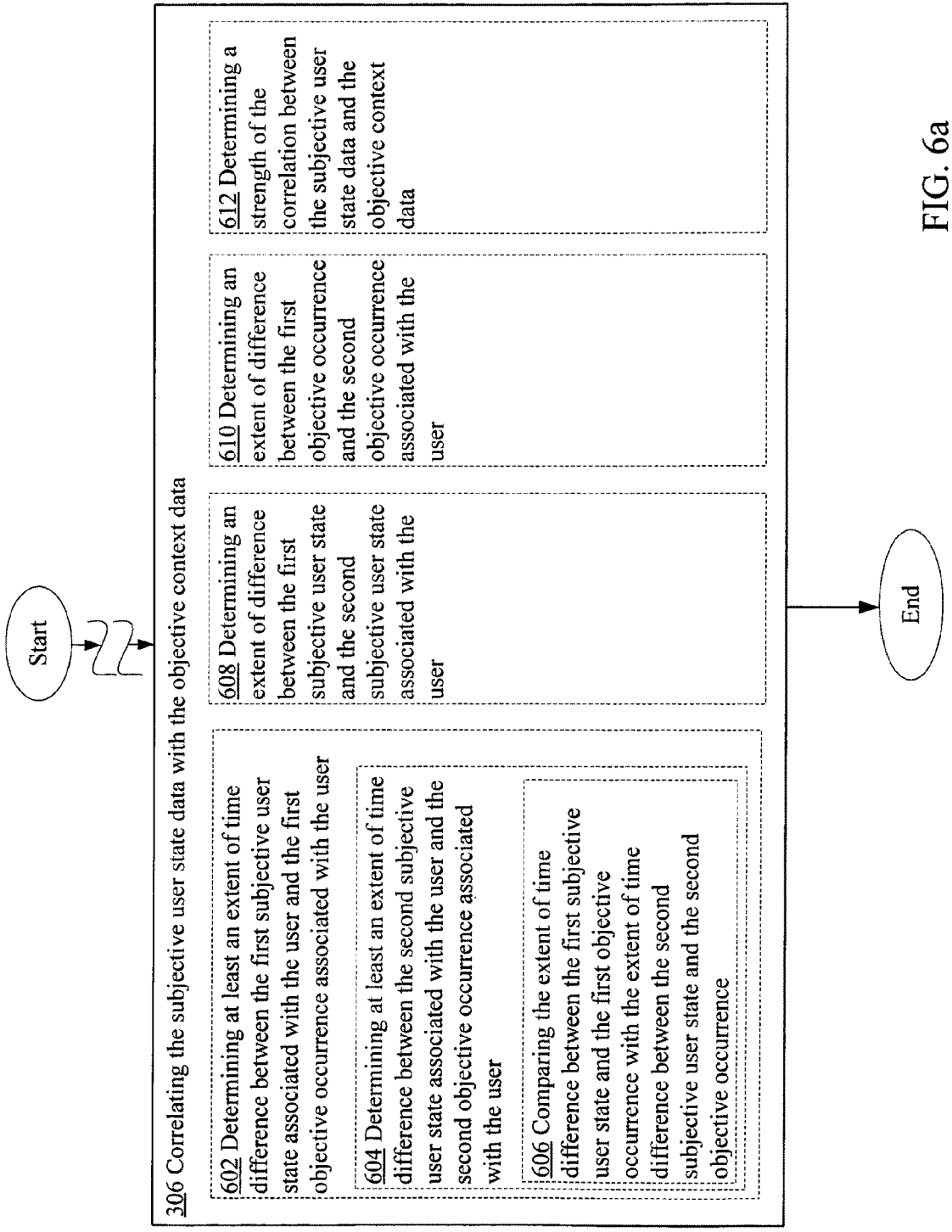
FIG. 6a is a high-level logic flowchart of a process depicting alternate implementations of the correlation operation 306 of FIG. 3.
Figure 6B:
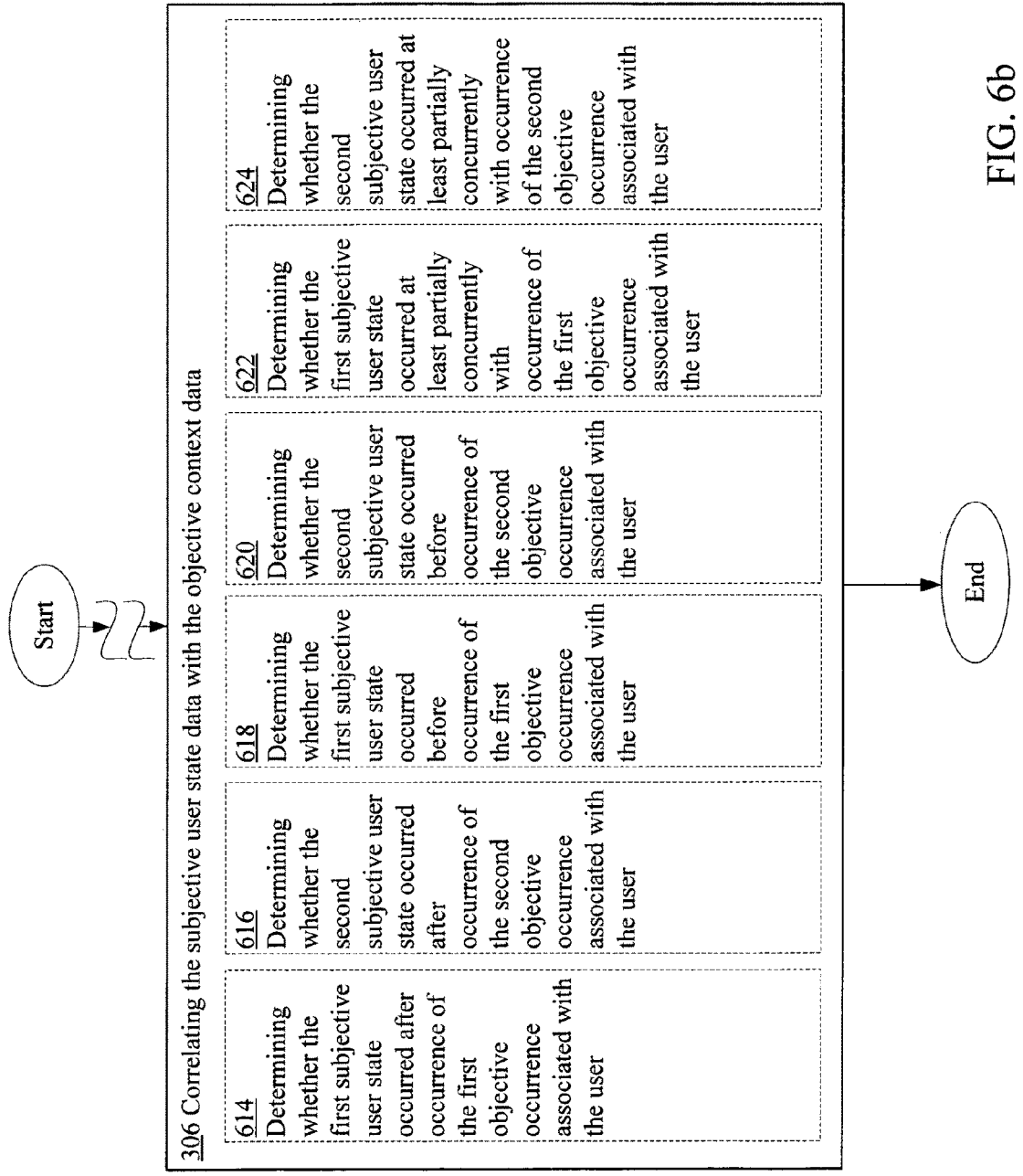
FIG. 6b is a high-level logic flowchart of a process depicting alternate implementations of the correlation operation 306 of FIG. 3.

Referring back to FIG. 3, the correlation operation 306 may include one or more additional operations as illustrated in FIGS. 6a and 6b. For example, in various implementations, the correlation operation 306 may include an operation 602 for determining at least an extent of time difference between the first subjective user state associated with the user and the first objective occurrence associated with the user as depicted in FIG. 6a. For instance, the subjective user state and objective occurrence time difference determination module 214 (see FIG. 2c) of the computing device 10 determining at least an extent of time difference between the occurrence of the first subjective user state (e.g., an extreme hangover) associated with the user 20* and the occurrence of the first objective occurrence (e.g., drinking four shots of whiskey) associated with the user 20* by, for example, comparing a time stamp associated with the first subjective user state with a time stamp associated with the first objective occurrence.

In some implementations, operation 602 may further include an operation 604 for determining at least an extent of time difference between the second subjective user state associated with the user and the second objective occurrence associated with the user as depicted in FIG. 6a. For instance, the subjective user state and objective occurrence time difference determination module 214 of the computing device 10 determining at least an extent of time difference between the second subjective user state (e.g., a slight hangover) associated with the user 20* and the second objective occurrence (e.g., again drinking two shots of whiskey) associated with the user 20* by, for example, comparing a time stamp associated with the second subjective user state with a time stamp associated with the second objective occurrence.

In some implementations, operation 604 may further include an operation 606 for comparing the extent of time difference between the first subjective user state and the first objective occurrence with the extent of time difference between the second subjective user state and the second objective occurrence as depicted in FIG. 6a. For instance, the comparison module 216 (see FIG. 2c) of the computing device 10 comparing the extent of time difference between the first subjective user state (e.g., an extreme hangover) and the first objective occurrence (e.g., drinking four shots of whiskey) with the extent of time difference between the second subjective user state (e.g., a slight hangover) and the second objective occurrence (e.g., drinking two shots of whiskey).

In various implementations, the correlation operation 306 may include an operation 608 for determining an extent of difference between the first subjective user state and the second subjective user state associated with the user as depicted in FIG. 6a. For instance, the subjective user state difference determination module 210 (see FIG. 2c) of the computing device 10 determining an extent of difference between the first subjective user state (e.g., an extreme hangover) and the second subjective user state (e.g., a slight hangover) associated with the user 20*. Such an operation may be implemented to, for example, determine whether there is a relationship between a subjective user state (e.g., a level of hangover) and an objective occurrence (e.g., amount of consumption of whiskey) or in determining a strength of correlation between the subjective user state and the objective occurrence.

In various implementations, the correlation operation 306 may include an operation 610 for determining an extent of difference between the first objective occurrence and the second objective occurrence associated with the user as depicted in FIG. 6a. For instance, the objective occurrence difference determination module 212 (see FIG. 2c) determining an extent of difference between the first objective occurrence (e.g., drinking four shots of whiskey) and the second objective occurrence (e.g., drinking two shots of whiskey) associated with the user 20*. Such an operation may be implemented to, for example, determine whether there is a relationship between a subjective user state (e.g., a level of hangover) and an objective occurrence (e.g., amount of consumption of whiskey) or in determining a strength of correlation between the subjective user state and the objective occurrence.

In various implementations, the correlation operation 306 may include an operation 612 for determining a strength of the correlation between the subjective user state data and the objective context data as depicted in FIG. 6a. For instance, the strength of correlation determination module 218 (see FIG. 2c) of the computing device 10 determining a strength of the correlation between the subjective user state data (e.g., hangover) and the objective context data (e.g., drinking whiskey).

In some implementations, the correlation operation 306 may include an operation 614 for determining whether the first subjective user state occurred after occurrence of the first objective occurrence associated with the user as depicted in FIG. 6b. For instance, the determination module 219 of the computing device 10 determining whether the first subjective user state (e.g., upset stomach) occurred after occurrence of the first objective occurrence (e.g., eating a banana) associated with the user 20* (e.g., determining whether the first subjective user state occurred within a predefined time increment after the occurrence of the first objective occurrence such as determining whether the first subjective user state occurring within 15 minutes, 30 minutes, 1 hour, 1 day, or some other time increment after the occurrence of the first objective occurrence).

In some implementations, the correlation operation 306 may include an operation 616 for determining whether the second subjective user state occurred after occurrence of the second objective occurrence associated with the user as depicted in FIG. 6b. For instance, the determination module 219 of the computing device 10 determining whether the second subjective user state (e.g., upset stomach) occurred after occurrence of the second objective occurrence (e.g., eating a banana) associated with the user 20* (e.g., determining whether the second subjective user state occurred within a predefined time increment after the occurrence of the second objective occurrence such as determining whether the first subjective user state occurring within 15 minutes, 30 minutes, 1 hour, 1 day, or some other time increment after the occurrence of the second objective occurrence).

In some implementations, the correlation operation 306 may include an operation 618 for determining whether the first subjective user state occurred before occurrence of the first objective occurrence associated with the user as depicted in FIG. 6b. For instance, the determination module 219 of the computing device 10 determining whether the first subjective user state (e.g., feeling gloomy) occurred before occurrence of the first objective occurrence (e.g., raining weather) associated with the user 20* (e.g., determining whether the first subjective user state occurred within a predefined time increment before the occurrence of the first objective occurrence such as determining whether the first subjective user state occurring within 15 minutes, 30 minutes, 1 hour, 1 day, or some other time increment before the occurrence of the first objective occurrence).

In some implementations, the correlation operation 306 may include an operation 620 for determining whether the second subjective user state occurred before occurrence of the second objective occurrence associated with the user as depicted in FIG. 6b. For instance, the determination module 219 of the computing device 10 determining whether the second subjective user state (e.g., feeling gloomy) occurred before occurrence of the second objective occurrence (e.g., raining weather) associated with the user 20* (e.g., determining whether the second subjective user state occurred within a predefined time increment before the occurrence of the second objective occurrence such as determining whether the second subjective user state occurring within 15 minutes, 30 minutes, 1 hour, 1 day, or some other time increment before the occurrence of the second objective occurrence).

In some implementations, the correlation operation 306 may include an operation 622 for determining whether the first subjective user state occurred at least partially concurrently with occurrence of the first objective occurrence associated with the user as depicted in FIG. 6b. For instance, the determination module 219 of the computing device 10 determining whether the first subjective user state (e.g., happiness) occurred at least partially concurrently with occurrence of the first objective occurrence (e.g., boss left town) associated with the user 20*.

In some implementations, the correlation operation 306 may include an operation 624 for determining whether the second subjective user state occurred at least partially concurrently with occurrence of the second objective occurrence associated with the user as depicted in FIG. 6b. For instance, the determination module 219 of the computing device 10 determining whether the second subjective user state (e.g., happiness) occurred at least partially concurrently with occurrence of the second objective occurrence (e.g., boss left town) associated with the user 20*.

Figure 7:
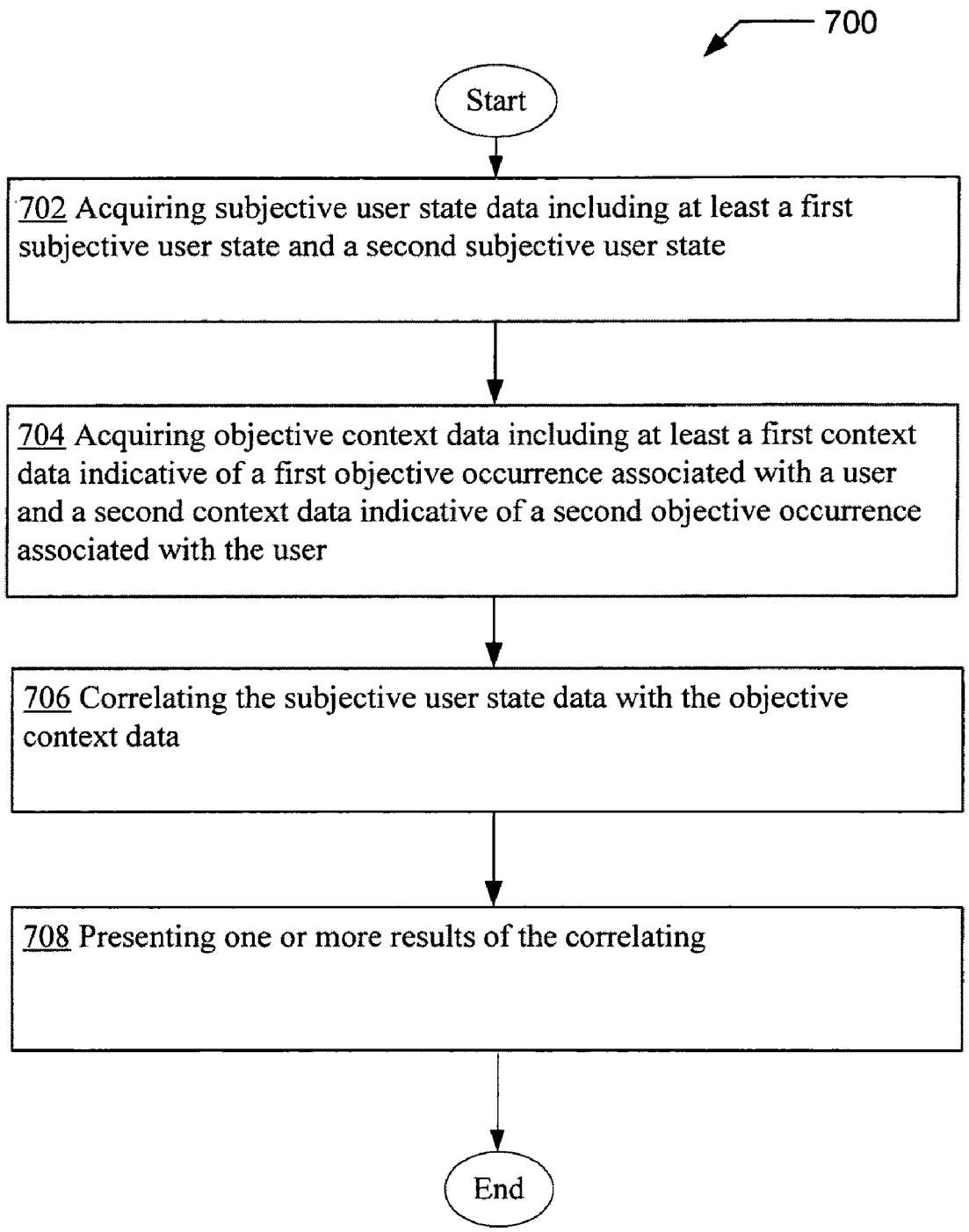
FIG. 7 is a high-level logic flowchart of another process.

FIG. 7 illustrates another operational flow 700 related to acquisition and correlation of subjective user state data and objective context data, and for presenting one or more results of the correlation in accordance with various embodiments. The operational flow 700 may include at least a subjective user state data acquisition operation 702, an objective context data acquisition operation 704, and a correlation operation 706 that corresponds to and mirror the subjective user state data acquisition operation 302, the objective context data acquisition operation 304, and the correlation operation 306, respectively, of the operational flow 300 of FIG. 3. In addition, operational flow 700 includes a presentation operation 708 for presenting one or more results of the correlating of the subjective user state data and the objective context data. For instance, the presentation module 108 of the computing device 10 presenting (e.g., displaying via the user interface 122 or transmitting via the network interface 120) one or more results of the correlating of the subjective user state data 60 with the objective context data 70*.

Figure 8A:
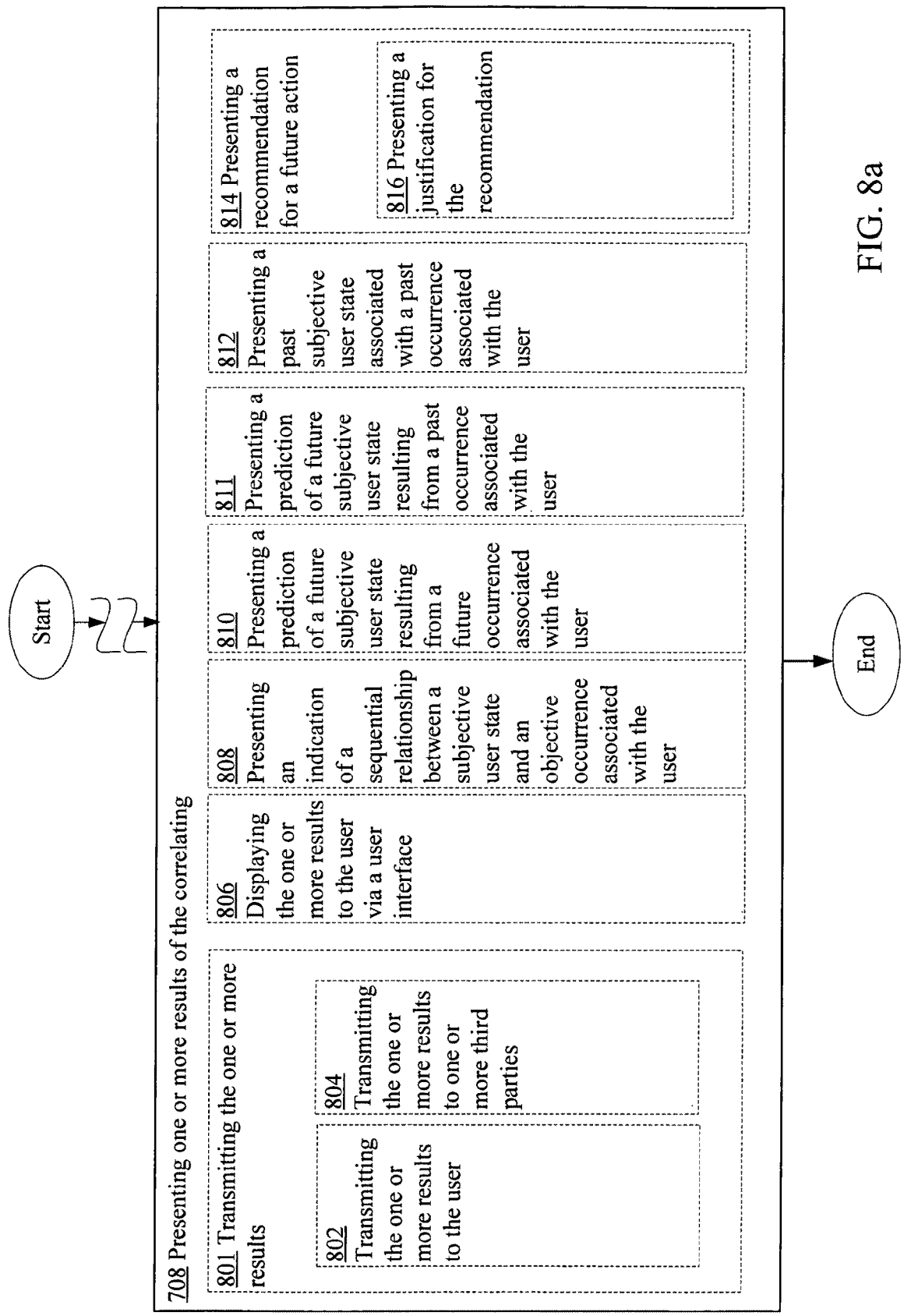
FIG. 8a is a high-level logic flowchart of a process depicting alternate implementations of the presentation operation 708 of FIG. 7.
Figure 8B:
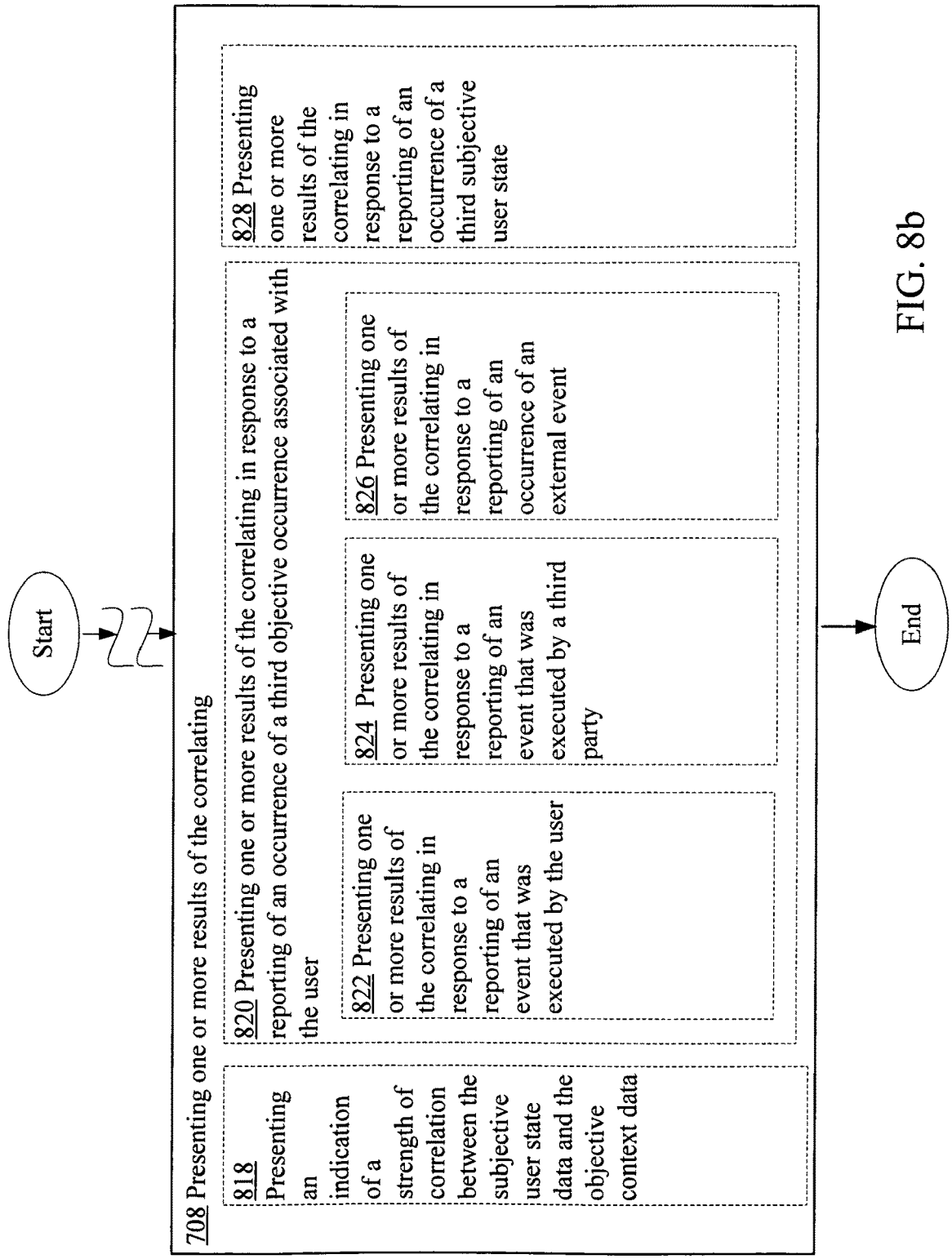
FIG. 8b is a high-level logic flowchart of a process depicting alternate implementations of the presentation operation 708 of FIG. 7.

The presentation operation 702 may include one or more additional operations in various alternative implementations as illustrated in FIGS. 8a and 8b. For example, in some implementations, the presentation operation 702 may include a transmission operation 801 for transmitting the one or more results as depicted in FIG. 8a. For instance, the transmission module 220 (see FIG. 2d) of the computing device 10 transmitting (e.g., via the network interface 120) the one or more results of the correlation of the subjective user state data with the objective context data.

In some implementations, the transmission operation 801 may include an operation 802 for transmitting the one or more results to the user as depicted in FIG. 8a. For instance, the transmission module 220 of the computing device 10 transmitting (e.g., via the network interface 120) the one or more results of the correlating of the subjective user state data 60 with the objective context data 70* to the user 20a.

In some implementations, the transmission operation 801 may include an operation 804 for transmitting the one or more results to one or more third parties as depicted in FIG. 8a. For instance, the transmission module 220 of the computing device 10 transmitting (e.g., via the network interface 120) the one or more results of the correlating of the subjective user state data 60 with the objective context data 70* to one or more third parties 50.

In some implementations, the presentation operation 708 may include an operation 806 for displaying the one or more results to the user via a user interface as depicted in FIG. 8a. For instance, the display module 222 (see FIG. 2d) of the computing device 10 displaying the one or more results of the correlating of the subjective user state data 60 with the objective context data 70* to the user 20* via a user interface 122 (e.g., display monitor and/or an audio device). Note that as used herein "displaying" may refer to the showing of the one or more results through, for example, a display monitor, and/or audibly indicating the one or more results via an audio device.

In some implementations, the presentation operation 708 may include an operation 808 for presenting an indication of a sequential relationship between a subjective user state and an objective occurrence associated with the user as depicted in FIG. 8a. For instance, the presentation module 108 of the computing device 10 presenting (e.g., via a network interface 120 or a user interface 122) an indication of a sequential relationship between a subjective user state (e.g., hangover) and an objective occurrence (e.g., consuming at least two shots of whiskey) associated with the user 20*. In this example, the presented indication may indicate that the user 20* will have a headache after drinking two or more shots of whiskey.

In some implementations, the presentation operation 708 may include an operation 810 for presenting a prediction of a future subjective user state resulting from a future occurrence associated with the user as depicted in FIG. 8a. For instance, the presentation module 108 of the computing device 10 presenting (e.g., via a network interface 120 or a user interface 122) a prediction of a future subjective user state (e.g., sadness) resulting from a future occurrence (e.g., missing son's football game) associated with the user 20*. In this example, the presented indication may indicate that the user 20* will be sad if the user misses his son's football game.

In some implementations, the presentation operation 708 may include an operation 811 for presenting a prediction of a future subjective user state resulting from a past occurrence associated with the user as depicted in FIG. 8a. For instance, the presentation module 108 of the computing device 10 presenting (e.g., via a network interface 120 or a user interface 122) a prediction of a future subjective user state (e.g., you will get a stomach ache) resulting from a past occurrence (e.g., ate a banana) associated with the user 20*.

In some implementations, the presentation operation 708 may include an operation 812 for presenting a past subjective user state associated with a past occurrence associated with the user as depicted in FIG. 8a. For instance, the presentation module 108 of the computing device 10 presenting (e.g., via a network interface 120 or a user interface 122) a past subjective user state associated with a past occurrence associated with the user 20* (e.g., "did you know that whenever the user drinks green tea, the user always feels alert?").

In some implementations, the presentation operation 708 may include an operation 814 for presenting a recommendation for a future action as depicted in FIG. 8a. For instance, the presentation module 108 of the computing device 10 presenting (e.g., via a network interface 120 or a user interface 122) a recommendation for a future action (e.g., "you should take a dose of brand x aspirin for your headaches"). Note that in this example, the consumption of the brand x aspirin is the objective occurrence and the stopping or easing of a headache is the subjective user state.

In particular implementations, operation 814 may further include an operation 816 for presenting a justification for the recommendation as depicted in FIG. 8a. For instance, the presentation module 108 of the computing device 10 presenting (e.g., via a network interface 120 or a user interface 122) a justification for the recommendation (e.g., "brand x aspirin in the past seems to work the best for your headaches").

In some implementations, the presentation operation 708 may include an operation 818 for presenting an indication of a strength of correlation between the subjective user state data and the objective context data as depicted in FIG. 8b. For instance, the presentation module 108 of the computing device 10 presenting (e.g., via a network interface 120 or a user interface 122) an indication of a strength of correlation between the subjective user state data 60 and the objective context data 70* (e.g., "you sometimes get a headache after a night of drinking whiskey").

In various implementations, the presentation operation 708 may include an operation 820 for presenting one or more results of the correlating in response to a reporting of an occurrence of a third objective occurrence associated with the user as depicted in FIG. 8b. For instance, the presentation module 108 of the computing device 10 presenting (e.g., via a network interface 120 or a user interface 122) one or more results of the correlating (e.g., going to Hawaii causes user's allergies to act up) in response to a reporting (e.g., via a microblog entry or by other means) of an occurrence of a third objective occurrence (e.g., leaving for Hawaii) associated with the user 20*.

In various implementations, operation 820 may include one or more additional operations. For example, in some implementations, operation 820 may include an operation 822 for presenting one or more results of the correlating in response to a reporting of an event that was executed by the user as depicted in FIG. 8b. For instance, the presentation module 108 of the computing device 10 presenting (e.g., via a network interface 120 or a user interface 122) one or more results of the correlating (e.g., drinking two or more shots of whiskey causes a hangover) in response to a reporting of an event (e.g., reporting a shot of whiskey being drunk) that was executed by the user 20*, In some implementations, operation 820 may include an operation 824 for presenting one or more results of the correlating in response to a reporting of an event that was executed by a third party as depicted in FIG. 8b. For instance, the presentation module 108 of the computing device 10 presenting (e.g., via a network interface 120 or a user interface 122) one or more results (e.g., indication that the user should not drive) of the correlating (e.g., vision is always blurry after being sedated by a dentist) in response to a reporting of an event (e.g., sedation of the user by the dentist) that was executed by a third party 50 (e.g., dentist).

In some implementations, operation 820 may include an operation 826 for presenting one or more results of the correlating in response to a reporting of an occurrence of an external event as depicted in FIG. 8b. For instance, the presentation module 108 of the computing device 10 presenting (e.g., via a network interface 120 or a user interface 122) one or more results of the correlating (e.g., indication that the user is always depressed after the stock market drops more than 500 points) in response to a reporting of an occurrence of an external event (e.g., stock market drops 700 points).

In various implementations, the presentation operation 708 may include an operation 828 for presenting one or more results of the correlating in response to a reporting of an occurrence of a third subjective user state as depicted in FIG. 8b. For instance, the presentation module 108 of the computing device 10 presenting (e.g., via a network interface 120 or a user interface 122) one or more results of the correlating (e.g., taking brand x aspirin stops headaches) in response to a reporting of an occurrence of a third subjective user state (e.g., user has a headache).

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

Those having skill in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.).

In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

What is claimed is:

1. A computationally-implemented method, comprising:
    acquiring subjective user state data including at least a first subjective user state and a second subjective user state;
    acquiring objective context data including at least a first context data indicative of a first objective occurrence associated with a user and a second context data indicative of a second objective occurrence associated with the user; and
    correlating the subjective user state data with the objective context data, wherein said correlating the subjective user state data with the objective context data is performed via at least one of a machine, article of manufacture, or composition of matter.

2. The computationally-implemented method of claim 1, wherein said acquiring subjective user state data including at least a first subjective user state and a second subjective user state comprises:
    receiving at least a first subjective user state.

3. The computationally-implemented method of claim 2, wherein said receiving at least a first subjective user state comprises:

receiving a first subjective user state via a first blog entry generated by the user.

4. The computationally-implemented method of claim 2, wherein said receiving at least a first subjective user state comprises:

receiving a first subjective user state via a status report generated by the user.

5. The computationally-implemented method of claim 2, wherein said receiving at least a first subjective user state comprises:

receiving a second subjective user state via a second blog entry generated by the user.

6. The computationally-implemented method of claim 2, wherein said receiving at least a first subjective user state comprises:

receiving a second subjective user state via a status report generated by the user.

7. The computationally-implemented method of claim 2, wherein said receiving at least a first subjective user state comprises:

receiving a first subjective user state that was obtained based, at least in part, on data provided by the user, the provided data indicating the first subjective user state associated with the user.

8. The computationally-implemented method system of claim 2, wherein said receiving at least a first subjective user state comprises:

receiving a first subjective user state indicating a subjective mental state of the user.

9. The computationally-implemented method system of claim 2, wherein said receiving at least a first subjective user state comprises:

receiving a first subjective user state indicating a subjective physical state of the user.

10. The computationally-implemented method system of claim 2, wherein said receiving at least a first subjective user state comprises:

receiving a first subjective user state indicating a subjective overall state of the user.

11. The computationally-implemented method of claim 2, wherein said receiving at least a first subjective user state comprises:

receiving a second subjective user state that was obtained based, at least in part, on data provided by the user, the provided data indicating the second subjective user state associated with the user.

12. The computationally-implemented method of claim 2, wherein said receiving at least a first subjective user state comprises:

receiving a second subjective user state indicating a subjective mental state of the user.

13. The computationally-implemented method of claim 2, wherein said receiving at least a first subjective user state comprises:

receiving a second subjective user state indicating a subjective physical state of the user.

14. The computationally-implemented method of claim 2, wherein said receiving at least a first subjective user state comprises:

receiving a second subjective user state indicating a subjective overall state of the user.

15. The computationally-implemented method of claim 1, wherein said acquiring subjective user state data including at least a first subjective user state and a second subjective user state comprises:

acquiring a first time stamp associated with the first subjective user state and a second time stamp associated with the second subjective user state.

16. The computationally-implemented method of claim 1, wherein said acquiring objective context data including at least a first context data indicative of a first objective occurrence associated with a user and a second context data indicative of a second objective occurrence associated with the user comprises:

receiving the objective context data.

17. The computationally-implemented method of claim 16, wherein said receiving the objective context data comprises:

receiving the objective context data via one or more blog entries.

18. The computationally-implemented method of claim 16, wherein said receiving the objective context data comprises:

receiving the objective context data via one or more status reports.

19. The computationally-implemented method of claim 16, wherein said receiving the objective context data comprises:

receiving the objective context data from one or more third party sources.

20. The computationally-implemented method of claim 16, wherein said receiving the objective context data comprises:

receiving the objective context data from one or more sensors configured to sense one or more objective occurrences associated with the user.

21. The computationally-implemented method of claim 16, wherein said receiving the objective context data comprises:

receiving the objective context data from the user.

22. The computationally-implemented method of claim 1, wherein said acquiring objective context data including at least a first context data indicative of a first objective occurrence associated with a user and a second context data indicative of a second objective occurrence associated with the user comprises:

acquiring a first context data indicative of a first activity performed by the user and a second context data indicative of a second activity performed by the user.

23. The computationally-implemented method of claim 1, wherein said acquiring objective context data including at least a first context data indicative of a first objective occurrence associated with a user and a second context data indicative of a second objective occurrence associated with the user comprises:

acquiring a first context data indicative of a first activity performed by a third party and a second context data indicative of a second activity performed by the third party.

24. The computationally-implemented method of claim 1, wherein said acquiring objective context data including at least a first context data indicative of a first objective occurrence associated with a user and a second context data indicative of a second objective occurrence associated with the user comprises:

acquiring a first context data indicative of a first physical characteristic of the user and a second context data indicative of a second physical characteristic of the user.

25. The computationally-implemented method of claim 1, wherein said acquiring objective context data including at least a first context data indicative of a first objective occurrence associated with a user and a second context data indicative of a second objective occurrence associated with the user comprises:
  acquiring a first context data indicative of a first external event and a second context data indicative of a second external event.

26. The computationally-implemented method of claim 1, wherein said acquiring objective context data including at least a first context data indicative of a first objective occurrence associated with a user and a second context data indicative of a second objective occurrence associated with the user comprises:
  acquiring a first time stamp associated with the first objective occurrence and a second time stamp associated with the second objective occurrence.

27. The computationally-implemented method of claim 1, wherein said correlating the subjective user state data with the objective context data comprises:
  determining whether the first subjective user state occurred after occurrence of the first objective occurrence associated with the user.

28. The computationally-implemented method of claim 1, wherein said correlating the subjective user state data with the objective context data comprises:
  determining whether the second subjective user state occurred after occurrence of the second objective occurrence associated with the user.

29. The computationally-implemented method of claim 1, wherein said correlating the subjective user state data with the objective context data comprises:
  determining whether the first subjective user state occurred before occurrence of the first objective occurrence associated with the user.

30. The computationally-implemented method of claim 1, wherein said correlating the subjective user state data with the objective context data comprises:
  determining whether the second subjective user state occurred before occurrence of the second objective occurrence associated with the user.

31. The computationally-implemented method of claim 1, wherein said correlating the subjective user state data with the objective context data comprises:
  determining whether the first subjective user state occurred at least partially concurrently with occurrence of the first objective occurrence associated with the user.

32. The computationally-implemented method of claim 1, wherein said correlating the subjective user state data with the objective context data comprises:
  determining whether the second subjective user state occurred at least partially concurrently with occurrence of the second objective occurrence associated with the user.

33. The computationally-implemented method of claim 1, further comprising:
  presenting one or more results of the correlating.

34. The computationally-implemented method of claim 33, wherein said presenting one or more results of the correlating comprises:
  transmitting the one or more results.

35. The computationally-implemented method of claim 33, wherein said presenting one or more results of the correlating comprises:
  displaying the one or more results to the user via a user interface.

36. The computationally-implemented method of claim 33, wherein said presenting one or more results of the correlating comprises:
  presenting an indication of a sequential relationship between a subjective user state and an objective occurrence associated with the user.

37. The computationally-implemented method of claim 33, wherein said presenting one or more results of the correlating comprises:
  presenting a prediction of a future subjective user state resulting from a future occurrence associated with the user.

38. The computationally-implemented method of claim 33, wherein said presenting one or more results of the correlating comprises:
  presenting a prediction of a future subjective user state resulting from a past occurrence associated with the user.

39. The computationally-implemented method of claim 33, wherein said presenting one or more results of the correlating comprises:
  presenting a past subjective user state associated with a past occurrence associated with the user.

40. The computationally-implemented method of claim 33, wherein said presenting one or more results of the correlating comprises:
  presenting a recommendation for a future action.

41. The computationally-implemented method of claim 40, wherein said presenting a recommendation for a future action comprises:
  presenting a justification for the recommendation.

42. The computationally-implemented method of claim 2, wherein said receiving at least a first subjective user state comprises:
  receiving a first subjective user state from at least one of a wireless network or a wired network.

43. The computationally-implemented method of claim 7, wherein said receiving a first subjective user state that was obtained based, at least in part, on data provided by the user, the provided data indicating the first subjective user state associated with the user comprises:
  receiving a first subjective user state that was obtained based, at least in part, on an audio entry provided by the user.

44. The computationally-implemented method of claim 7, wherein said receiving a first subjective user state that was obtained based, at least in part, on data provided by the user, the provided data indicating the first subjective user state associated with the user comprises:
  receiving a first subjective user state that was obtained based, at least in part, on an image entry provided by the user.

45. A computationally-implemented system in the form of a machine, article of manufacture, or composition of matter, comprising:
  means for acquiring subjective user state data including at least a first subjective user state and a second subjective user state;
  means for acquiring objective context data including at least a first context data indicative of a first objective occurrence associated with a user and a second context data indicative of a second objective occurrence associated with the user; and
  means for correlating the subjective user state data with the objective context data.

* * * * *

UNITED STATES PATENT AND TRADEMARK OFFICE
CERTIFICATE OF CORRECTION

PATENT NO. : 8,046,455 B2  
APPLICATION NO. : 12/313659  
DATED : October 25, 2011  
INVENTOR(S) : Firminger et al.

Page 1 of 1

It is certified that error appears in the above-identified patent and that said Letters Patent is hereby corrected as shown below:

Column 33 line 29 claim 8 "The computationally-implemented method system of" should read --The computationally-implemented method of--

Column 33 line 34 claim 9 "The computationally-implemented method system of" should read --The computationally-implemented method of--

Column 33 line 39 claim 10 "The computationally-implemented method system of" should read --The computationally-implemented method of--

Signed and Sealed this
Seventeenth Day of January, 2012

David J. Kappos
*Director of the United States Patent and Trademark Office*